(12) United States Patent
Figueroa Saavedra

(10) Patent No.: US 12,082,956 B2
(45) Date of Patent: Sep. 10, 2024

(54) INTEGRAL SYSTEMS OF ORTHOVOLTAGE SOURCES THAT INDUCE IONIZING RADIATION

(71) Applicant: UNIVERSIDAD DE LA FRONTERA, Temuco (CL)

(72) Inventor: Rodolfo Gabriel Figueroa Saavedra, Temuco (CL)

(73) Assignee: UNIVERSIDAD DE LA FRONTERA, Temuco (CL)

( * ) Notice: Subject to any disclaimer, the term of this patent is extended or adjusted under 35 U.S.C. 154(b) by 227 days.

(21) Appl. No.: 17/641,613

(22) PCT Filed: Sep. 9, 2020

(86) PCT No.: PCT/IB2020/058387
§ 371 (c)(1),
(2) Date: Apr. 29, 2022

(87) PCT Pub. No.: WO2021/048764
PCT Pub. Date: Mar. 18, 2021

(65) Prior Publication Data
US 2022/0323026 A1 Oct. 13, 2022

Related U.S. Application Data

(60) Provisional application No. 62/897,730, filed on Sep. 9, 2019.

(51) Int. Cl.
*A61B 6/00* (2024.01)
*A61B 6/10* (2006.01)
(Continued)

(52) U.S. Cl.
CPC ............ *A61B 6/4007* (2013.01); *A61B 6/107* (2013.01); *A61B 6/485* (2013.01); *A61N 5/1049* (2013.01);
(Continued)

(58) Field of Classification Search
None
See application file for complete search history.

(56) References Cited

U.S. PATENT DOCUMENTS 9,739,729 B2 * 8/2017 Feser ................... G01N 23/223
2016/0252471 A1 9/2016 Guo et al.
2017/0234814 A1 8/2017 Ogata et al.

FOREIGN PATENT DOCUMENTS

| CN | 109709127 A | 5/2019 |
|---|---|---|
| CN | 110083091 A | 8/2019 |
| WO | 2008125680 A1 | 10/2008 |

OTHER PUBLICATIONS

R.G. Figueroa, et al; Optimal configuration for detection of gold nanoparticles in tumors using KB X-ray fluorescence line; Radiation Physics and Chemistry; vol. 117; Aug. 2015; pp. 198-202.
(Continued)

*Primary Examiner* — Hoon K Song
(74) *Attorney, Agent, or Firm* — LUCAS & MERCANTI, LLP

(57) ABSTRACT

A system for detecting, obtaining images and treating or eliminating tumours, diseases or other anomalies, excited by X-rays biomarked with metallic nanoparticles having an external support with a shield having a confocal system with a shielded external structure containing a convergent scan X-ray, a detection system, a second convergent treatment device connected to the confocal structure, and a supporting structure that contains the convergent scan X-ray device, the detection system and the second convergent treatment device; a controlled 3D scanning structure that moves a bed and/or focal point; an electronic control system with programmable electronics allowing operation of the convergent beam device, of the sensors and the movements of the 3D scanning system; and a computed tomography (CT) device with collimators, an X-ray tube and sensors.

23 Claims, 19 Drawing Sheets

(51) Int. Cl.
*A61B 6/40* (2024.01)
*A61N 5/10* (2006.01)
(52) U.S. Cl.
CPC .... *A61N 5/1084* (2013.01); *A61N 2005/1061* (2013.01)

(56) References Cited

OTHER PUBLICATIONS

International Search Report for Corresponding International Application No. PCT/IB2020/058387 dated Dec. 29, 2020 and English translation.

* cited by examiner

A　　　　　　　B

A　　　　　　　B

INTEGRAL SYSTEMS OF ORTHOVOLTAGE SOURCES THAT INDUCE IONIZING RADIATION

CROSS REFERENCE TO RELATED APPLICATION

This Application is a 371 of PCT/IB2020/058387 filed on Sep. 9, 2020, which claimed priority of U.S. Provisional Application No. 62/897,730, filed Sep. 9, 2019, each of which are incorporated herein by reference.

BACKGROUND OF THE INVENTION

The present invention relates to the medical industry and the X-ray fluorescence application industries. In particular, the present invention relates to a system and method for detecting, obtaining images and treating or eliminating neoplasms, pathologies or other anomalies, which is excited through X-rays biomarked with metallic nanoparticles.

The characterization, visualization and precise location of a tumor are very important aspects for the diagnosis and treatment of cancer. X-rays have been used for decades for this purpose. However, because X-rays provide contrast images of mainly dense (bone) tissue and very little soft tissue, it is necessary to use contrast enhancement methods to see soft tissue more clearly and in more detail and to view soft tissue from various angles in order to spatially detect a soft tissue tumor. Although X-rays are not currently used for precise three-dimensional localization, they are nonetheless considered one of the most important general-purpose diagnostic imaging techniques. It is important to remember that the excessive use of X-rays generates harmful effects to health, hence the importance of using the lowest possible power, to reduce the adverse effects and concentrated and focused on only the areas to be treated, so as not to damage adjacent tissue areas.

Computerized axial tomography (CAT), more commonly known as computerized tomography, revolutionized the field of clinical imaging. This technique, invented by Hounsfield in 1967, was a significant advance in the area, since it allows the visualization of images of tomographic anatomical slices.

Subsequently, high-quality 3D images were achieved thanks to the development of reconstruction software. In addition, by incorporating new and improved detectors (amorphous silicon, flat screen, CCD) and new contrast media, the quality of this technique has been optimized, obtaining images with a spatial resolution close to 1 mm. With this technique it is possible to accurately determine the position of the organs, and the presence of potential tumor tissue, which are later confirmed with other analyses, however, and despite the use of contrast materials, this still remains a shortcoming of the CAT technique.

Although nuclear magnetic resonance was developed by Rabi in 1938, its evolution began as a tomography imaging technique and was applied to humans only from the 1980s onwards. This meant an important advance in the field of medical imaging, since there was a notable improvement in contrast and with a better spatial resolution compared to the CAT technique, however, CAT is a much faster technique and in general is still massively valid.

From a functional point of view of tumor activity, the application of nuclear physics to medicine has provided two important techniques, which have produced notable developments. These are the SPECT (Single photon emission computerized tomography) and PET (Positron emission tomography) techniques, both implant a radiopharmaceutical. The SPECT technique is based on the nuclear decay emitted by a single gamma photon, which is detected by a gamma camera to determine the position of the point of emission of the photon and record it spatially with a resolution of 2-3 mm. This spatial precision depends on the optics and detection system of the gamma camera. In contrast, the PET technique is based on nuclear decay emitted by a positron, which then annihilates with an electron, emitting two anti-parallel photons. These photons are detected by a coincidence system that is capable of measuring an emission point and registering it spatially with a resolution of 2-4 mm. Although the measurement is greater than that obtained with the SPECT technique, PET detects tumors more efficiently because neoplastic tissues show a high metabolism with the glucose used as a carrier of the radiotracer associated with this technique.

The use of anatomical images fused with functional images, such as PET-NR, SPEC-CT and PET-CT, has recently produced a remarkable improvement in diagnosis. This is especially significant considering that the PET-CT technique is one of the most widely used and effective techniques, in which the functional characteristic is provided by the PET technique and the anatomical characteristic is provided by the CT technique. These fusion techniques have a spatial precision provided mainly by the precision of the anatomical technique. Savings in terms of time, positioning and space are achieved through the use of fusion. However, the use of two techniques, although they can be used very close together, is still very expensive and involves double radiation.

Functional images provide less precision than anatomical images, since they require a detection system capable of determining the location of the emission point of gamma photons (SPECT and PET, respectively). In addition, the use of a radiotracer means that not only the affected area is exposed to radiation, but also the entire body.

Among the known prior art is U.S. Pat. No. 9,739,729B2, which discloses a correlative evaluation of a sample using a combined X-ray computerized tomography (CT) and X-ray fluorescence (XRF) system and method for analyzing a sample using X-ray CT and XRF. The CT/XRF system includes an X-ray CT subsystem for volume information acquisition and a confocal XRF subsystem for characterizing elemental composition information. Geometric calibration is performed between the XRF subsystem and the X-ray CT subsystem so that a region of interest defined during X-ray CT acquisition can be retrieved by the XRF subsystem for subsequent XRF acquisition. The system combines the submicron spatial resolution 3D imaging capability of X-ray CT with the elemental composition analysis of confocal XRF to provide 3D elemental composition analysis of a sample with ppm-level sensitivity. This is applicable to many scientific research and industrial applications, an excellent example of which is the elemental identification of precious metal grains in crushed and ground ores and flotation tailings in the mining industry, but this system is for volumes as small as 100 microns. cubic, with voltages of the order of 17 keV and takes a long time, 173 hours.

In summary, current functional imaging systems, such as gamma SPECT and PET, are spatially imprecise and require the injection of a radioactive material, causing various harms to the people treated.

The degree of precision of the emission point of the radiotracer in the SPECT and PET techniques is established by the optics, the detector system and computer analysis, the latter of which triangulates the emitted signals. The location of the point is therefore indirect and statistical.

As far as full-body applications are concerned, PET MRI could be considered the state of the art in medical imaging today, its strengths can be summarized in three.
1. Soft tissue contrast in various areas of the body is superior to that achieved with CT.
2. Allows dynamic and morphological/joined temporal registration of functional data (dual).
3. The patient's radiation exposure can be substantially reduced.

Thanks to these and other qualities, the PET-MRI technique is having a greater demand and surpasses the modern PET-CT technique. However, the associated costs are still very high.

The use of metallic nanoparticles as biomarkers has been developing in order to achieve functional XFCT images in rats and as dose-enhancing agents when radiation is applied to the area. We have also found some documents that describe the use of low energy and orthovoltage X-ray beams towards a tumor area with nanoparticles infused in the tumor tissues, but with a different application form and a very different device than the one described below.

The big problem to solve is the detection of fluorescent signals emitted from inside the body, it is the poor signal to noise ratio, due to the fact that the fluorescent signal when induced from a source of X-radiation or γ external, and this results in high radiation scattering due to the Compton effect, which drastically reduces the fluorescent signal to be detected, especially if the matrix is based on light elements such as water.

Obtaining improved spatial resolution would be possible with a detection system in which the point of interest is pre-marked by the tumor biomarkers, directly capturing the induced fluorescent signal coming from there, without the need for a position-sensitive detector. This can only be done with a convergent X-ray beam focused on a point of interest positioned with millimeter precision in which characteristic high-energy radiation (~50 to 90 KeV) is induced. The fluorescent signal can escape from the body and be easily detected with an energy-resolving detector in confocal mode.

The confocal mode consists in that the X-ray source and the detector are pointing at the same focal point, that is, in this way it is possible to spatially fix the excitation and study point from the outside, reducing the signal-to-noise ratio. In this way it is possible to concentrate the radiation at that point, induce characteristic X-rays there, which are emitted in an isotropic mode and with the confocal detector the signal coming from there is captured. In this mode the signal to noise ratio is increased compared to a conventional mode, i.e. compared to an excitation with a non-convergent beam and detection without reference to position or excitation point.

Standard confocal techniques are used with visible light and low-energy (soft) X-rays on small samples, showing excellent results, especially in the field of microscopy. In the case of soft X-rays (5-20 keV), these use poly-capillaries to achieve the confocal mode, both for the X-ray source and for the detector, and allow the analysis of very small millimeter specimens.

According to the previous state it has been possible to develop a large confocal device with X-ray energy in the orthovoltage range through the detection of characteristic radiation K of elements with atomic number Z>50.

To solve the technical problem posed, the present system and method uses a convergent X-ray beam of greater energy and size instead of the one used by the conventional confocal technique, which allows its intensity to be concentrated at a greater depth (of several centimeters depending on the sample) and a large-area detector in confocal mode.

The higher energy and the larger size allow to increase the sensitivity for the detection of elements that are deeper within a given material matrix.

This detection, imaging and associated processing device to sweep the target with the focus/focal point of the confocal system and the X-rays of the target emerge from the array with an acceptable signal to noise ratio, which is why confocal geometry is important, as it improves the signal to noise ratio.

A proper X, Y, Z positioning system plus a large area photon detector could accurately map and detect certain chemical elements present in large sample sizes. Its spatial precision depends on the size of the focus/focal point and the precision of the positioning system, being able to reach sub-millimeter.

Furthermore, the use of a non-radioactive biomarker increases the generation of characteristic radiation in the X-ray excited zone. A suitable 3D scan of the focal point of the convergent beam around the area of interest and a confocal detection system for the emitted characteristic X-rays would allow to reconstruct a 3D EDXRF (Energy dispersive X-ray fluorescence, which corresponds to energy dispersive X-ray fluorescence) medical image, mainly associated with the main biomarker element.

Taking into consideration the state of the art of current medical imaging and radiation therapy systems, the invention presented here is based on the following aspects:
1. Capacity detection and visualization of chemical elements in the organism.
2. Existence of EDXRF imaging devices.
3. Convergent X-ray beam device or fluence concentrator at a focus.
4. Metallic biomarkers capable of selectively adhering to neoplastic cells.
5. Detection of the characteristic radiation induced in the biomarker at the excited focal point.
6. The focal point can be sub-millimeter in size.
7. High-energy X-ray fluorescence induced at the focal point and is capable of emerging from material from a depth of several cm.
8. The detection of the transmitted X-photons is related to the attenuation coefficients, particularly of the emission point material.
9. Detection can be performed with scintillation or solid-state detectors with high quantum efficiency and adapted to the energy of the X-rays to be detected.
10. The biomarker element of an area of interest, within a large sample size (geometric-specific object, "fantoma"), (100 ppm).
11. A detection system in confocal mode maximizes the fluorescent signal generated so that it is possible to detect at low concentration levels several cm deep.
12. The spatial position of the focal point is known in advance, so no external system is required to determine the spatial position of the signal emitted from it.

The foregoing configures a theranostic system and method that identifies and eliminates at least one tumor in a single process.

Convergent X-Ray Beam Device

As mentioned in the previous point, the 3D EDXRF confocal technique is only applicable to small material objects (measuring a few millimeters or less) due to the interest in using it as a microscope (μXRF).

If the sample is larger, the characteristic X-rays induced in the area of focus may self-absorb into the material. Furthermore, poly-capillary optics do not respond to energies above 50 keV. This limits deep applications in large sample sizes in biomedical or industrial fields, excluding the analysis of light and intermediate elements in the periodic table.

This invention uses one or more convergent beam reservoirs of energy in the radiodiagnostic range and orthovoltage.

Elemental Chemical Biomarkers

Obtaining or distributing 3D images of certain chemical elements located in a large material matrix requires a higher energy X-ray source, whose beam must reach the element(s) of interest in deep layers of the material. This is where the highest energy characteristic radiation is generated.

A review of the NITS tables of the water attenuation coefficient was carried out, applying Lambert's Law of Attenuation and determining the percentages of fluorescence reduction associated with different chemical elements of interest that could be found within the matrix. This was done in order to estimate what percentage of fluorescence radiation from a specific chemical element could come from inside a material matrix. Table 1 was built on this information. It shows various percentages of characteristic attenuation of photons of certain elements of the periodic table, emitted at different depths in a matrix of water.

| Atomic number Z | Element | Energy kα keV | Attenuation Coefficient $cm^2/g$ | Transmission % Thickness | | |
|---|---|---|---|---|---|---|
| | | | | 1 cm % | 5 cm % | 10 cm % |
| 43 | Technetium | 18.41 | 1.09E+00 | 33.9 | 0.68 | 0.01 |
| 53 | Iodine | 28.61 | 4.62E−01 | 66.3 | 12.8 | 1.6 |
| 55 | Cesium | 30.97 | 3.76E−01 | 69.6 | 15.4 | 2.7 |
| 64 | Gadolinium | 42.98 | 2.54E−01 | 77.5 | 28.1 | 7.8 |
| 79 | Gold | 68.78 | 1.95E−01 | 82.3 | 37.7 | 14.2 |
| 83 | Bismuth | 77.09 | 1.87E−01 | 82.9 | 39.1 | 15.3 |

A final important aspect to take into account is the null or very low concentration of elements that could be detected in the organ or object of interest. An out-of-area marking should be considered, whereby a carrier would transport the aforementioned element through the bloodstream and concentrate on the area of interest. This would allow the increase of the fluorescent signal in the area.

As seen in the Table, there are several elements that can be detected in depth through their characteristic lines Kα and Kβ. There are some that are currently in use, either as biomarkers or contrast media, such as iodine; or as agents that could be applied to see tumor activity, such as rubidium, technetium, gadolinium or gold, among others. The above elements could serve in this way, since they can adhere to specific neoplastic antibodies that are concentrated in the tumor area and, therefore, with the use of the invention proposed here, it will be possible to detect characteristic X-rays high energy, and a 3D scan of the entire tumor area can be performed. After a computer reconstruction process, a functional image of tumor activity can be obtained with visualization of the marker element similar to that obtained with PET or SPECT techniques, although in the reconstruction process there would be better spatial resolution.

In recent years, interest has increasingly focused on nanoparticles rather than other important tracer elements. The vascular permeability in a human tumor is around 400 nm, so nanoparticles can enter through the bloodstream and can accumulate within a tumor by the mere fact of increased perfusion in tumor activity, which is enhanced when nanoparticles are bound to particular antigens.

Gold nanoparticles, gold nano_particles (GNP), have properties such as biocompatibility, high atomic number (high-Z) and the ability to bind to anti-tumor agents. The above properties also imply that GNPs have potential as contrast agents, increasing the absorption of photoelectric photons and the accuracy of tumor diagnosis. At energies above 100 keV, the bulk attenuation of gold is higher than that of iodine, showing that a better contrast with gold will be achieved. Recent studies have used GNP as marker agents in vivo.

Tumor Detection, Imaging and Treatment Device

This invention consists of a device for detecting, functional imaging and treating of neoplasms that excites with X-rays deep tumors biomarked with metallic nanoparticles using a convergent device that concentrates the fluence of ionizing radiation at a point, the excitation applied there generates secondary radiation formed by X-ray fluorescence and electrons (photo electrons and Auger electrons). The first of this secondary radiation can escape volume and be detected externally by means of a solid-state detection device and account for the position from the position of the concentration point that is defined from the outside thanks to a 3D positioning system controlled by stepper motors and software. For their part, the electrons can deposit doses in the same concentration point where they are generated. A 3D scan of the focal point of the applied radiation of a given area of interest allows the acquisition of a matrix that associates a spatial coordinate to a characteristic spectrum or to the beads associated to the characteristic peak area(s) associated to the biomarker element. As the scan progresses, the image is automatically and simultaneously reconstructed by scanning and control software. At each scanning point of the convergent beam where the biomarker is present, there will be a count of the characteristic photons of the biomarker, which will give a numerical value associated with a certain concentration intensity of the biomarker in the neoplasm and if this is not present, there will be no count there.

In addition, a second, higher intensity confocal convergent device can annihilate the neoplastic cells, thus initiating the treatment process simultaneously, a fast radiation beam switch, through a barrier that cuts the beam.

APPLICATION EXAMPLES

In addition to the applications in living beings such as the one described above, this invention was used as a scanner in inanimate objects, as an airport security element, cavity detection, elemental composition of objects inside a suitcase, deep structural failures of parts or apply it to kill bone infections, to apply a convergent beam in an artery to kill neoplastic cells because they have greater radio sensitivity than healthy cells. This device was used with a convergent dynamic scanning device (150), which had a power of 30 W and 30 kVolt with 1 mA, managing to detect in water-filled "fantoma"-type mannequins with 10 cm in diameter, presence of gold nanoparticles, used as a biomarker, detecting the presence of nanoparticles in concentrations of %5 w/w in a water matrix and finding the tumor at a depth of 5 cm, which was subsequently scanned by the convergent treatment device (300).

DETAILED DESCRIPTION OF THE INVENTION

A device for detecting, imaging and treating theranostic neoplasms that excites with X-rays deep tumors biomarked with metallic nanoparticles consists of four main parts:
- A. A confocal system (1000) comprising:
  - scanning X-ray convergent device 100.
  - detection system 200 for X photons with collimators solidary/integral/jointly and confocal to the first device,
  - convergent treatment device 300 solidary with the confocal structure 100 and 200,
  - supporting structure 400 that contains the three previous elements.
- B. A 3D motion controlled structure 500 moving a stretcher and/or focal point where the ionizing radiation is concentrated,
- C. An external shielded support structure 600 containing all of the above components.
- D. An electronic system and control method,
  - a. programmable electronics 700 allowing the operation of the convergent beam device, the operation of the detectors and the movements of the 3D scanning system,
  - b. a control method that is executed in a computer 800 that connects and controls the positioning system for tumor location and scanning with the X-ray generation equipment and the detection system, the convergent treatment device and the fast gates,
- E. A computerized tomography CT (2000) formed by: collimators, X-ray tube and detectors is incorporated in the same structure 600.

A.—Confocal System (1000)

This device comprises four fundamental elements that shape the confocal structure in which the convergent beam of the scanning device 100 shares the same focal point that the detection system 200 focuses on, and the convergent treatment device 300 may or may not share the same focal point. These three elements joined by a supporting structure 400, which contains them solidary/jointly. FIG. 1.

a. Exploration/scanning convergent device (100)

It is a convergent beam device that concentrates the radiation flux at a focal point located in the focal zone (target). This can be dynamic or static, a. Static convergent option The static option consists of a large convergent X-ray tube 100, consisting of an electron gun 1, a beam braker 2, a vacuum cylinder 3 with cylindrical anode on its inner side 4 whose X-ray output is through the front of the cylinder and is collimated by means of a spherical poly collimator 5 whose holes or septa 6 point in the direction of a focal point which may or may not be fixed to the structure, a laser guide assembly 7 allows its location 500; FIG. 2. It is worth mentioning that the septa homogenize the exit direction of a beam or allow only the photons that go in the direction of said holes to pass.

The dynamic option consists of elemental dynamic with supporting arch arm 8, rotation shaft 9, bearing 10, laser guide bar 11, X-ray tube, collimator 13, counterweight 14 and clamp support 400; FIG. 3

Another static convergent beam device option is formed by a curved anode cylinder 16; FIG. 3.

Another static convergent beam device option is formed by a curved anode ring 17; FIG. 4.

Another static convergent beam device option is formed by a long curved cylinder as the anode 18; FIG. 6.

b. Dynamic convergent option

The dynamic option consists of an X-ray tube 12 rotating through a C-shaped arc whose X-ray output is collimated by means of a collimator 13 pointing in the direction of a focal point, center of the radius of curvature of the C, which is fixed or movable with respect to the structure 500; FIG. 5.

Another dynamic option can contain a C with shaft/axis and with fixed holes 19 in different positions that allow to fix the angle of the convergent cone generated in preset positions; FIG. 7.

Another dynamic option can contain the X-ray tube 12 and the counterweight 14, a C with long curved slots 20 with shafts 9 with pin 21 that allow to fix the angle of the convergent cone generated in continuous positions and mechanical tightening of fixation; FIG. 8.

Another dynamic option may contain a C with curved toothed slots 22, shaft 9 and an electric motor 23 that allow the angle of the convergent cone to be varied by moving the tube in the direction of the C, generated in a continuous mode; FIG. 9.

Another dynamic option can contain a straight arm 24 with shaft 9, with radius and angle of the convergent cone generated regulated by angular fixation 25; FIG. 10.

Another dynamic option can contain a straight arm with shaft, with fixed holes 19 in different positions that allow to fix the angle of the convergent cone generated; FIG. 11.

Another dynamic option can contain a straight arm with a shaft, which allows the angle of the convergent cone to be varied by means of electric motors 26; FIG. 12.

Another dynamic option may contain a straight arm with a toothed straight slot shaft 27, which allows the angle and position of the convergent cone to be varied by means of the radial and angular movement of the ray tube outlet with two electric motors 28, FIG. 13.

b. Detection system (200)

The confocal detection system 200 of the device (1000) comprises: a confocal collimation unit 29 one or more detectors 30 with energy resolution for the detection of K lines of heavy elements, electronic pulse processing units (amplification and conformation) 31 and multichannel 32; FIG. 14.

One option of the detection system is to have a confocal collimation unit formed by a set of straight septa 33. FIG. 15.

One option of the detection system is to have a confocal collimation unit formed by a set of conical septa 34. FIG. 16.

An option of the detection system is formed by a set of conical honeycomb collimators 35. FIG. 17.

One option of the detection system is that it consists of a set of solid-state confocal detectors of the CdTe 36 (cadmium telluride) type on supports 37 that allow the detection of K photons from heavy elements. FIG. 18.

Another option of the detection system is that it consists of NaI(Tl) scintillator detectors that allow the detection of K photons from heavy elements.

One option of the detection system is that it consists of solid-state Ge (Germanium) detectors that allow the detection of K photons from heavy elements.

One option of the detection system consists of a set of scintillator detectors, which allow the detection of K photons from heavy elements over a large area. FIG. 19.

One option of the detection system consists of a large-area solid-state detector array, which allows the detection of K photons from heavy elements. FIG. 20.

c. Convergent treatment device (300)

The treatment device is a convergent output device 40 very similar to that of the previous exploratory/scanning device in a dynamic or fixed version that, unlike the latter, operates at a higher power, its focal point may or may not be confocal with the first devices (100 and 200) or go slightly offset from this. A fast on/off action of the beam is highly necessary; therefore, this device (300) must be permanently on and has a fast gate for complete attenuation (<1%) of the beam formed by metal foils 41 (FIG. 21), which activates the beam output only when there is a fluorescent signal by opening it with a bidirectional solenoid 42. FIG. 21. An option for the static convergent treatment device 40 is with double gate 41 for full attenuation (<1%) activated by solenoid 42, FIG. 22.

An option for the static convergent device treatment 40 is with circular spherical gate with holes 47 for full attenuation (<1%) activated by central stepper motor, FIG. 23.

An option for dynamic convergent treatment device, treatment X-ray tube 47, gated for full attenuation 41 (<1%), solenoid driven 42 with attachment to collimator 48 FIG. 24.

d. Supporting structure (400)

The supporting structure 400 is the structure that jointly contains the convergent exploratory/scanning beam 100, the confocal detector 200 and the aforementioned treatment convergent beam 300, where the three fundamental elements of this invention are supported in confocal mode.

Another option of the support structure for Cartesian scanning 410 is formed by the support base 50 for detector supports 36 and the structure 51 that contains the rotating support arch 8, which on its opposite sides has the supports 15 for the X-ray tubes to generate the convergent scanning beam 150 and the supports 15 for the X-ray tube to generate the convergent treatment beam 300, the whole assembly supported on legs 49 (FIG. 25).

Another option of the Cartesian support structure 410 may also house static convergent exploratory/scanning and treating devices or a combination of static and dynamic devices.

Another option of the Cartesian support structure 410 can also house an X-ray tube for exploration 12 and another for treatment 40 in a dynamic configuration 150 (FIG. 26) in the same rotating support arch.

Another option of the support structure 400 for cylindrical sweeping is formed by a base arch 55 that contains the fixing elements 56 for the three essential elements (FIG. 27).

Another option of the support structure has a longer arch 57 and can house a second detector 38 at its other end (FIG. 28).

Another option of the cylindrical support structure can also house dynamic convergent devices (FIG. 29).

Another option of the cylindrical support structure can also house a combination of dynamic or static convergent devices.

B. 3D Motion Structure 500

The 3D motion device 500 is the one that allows the spatial scanning of a stretcher and/or focal point, so that there is a relative movement of the focal point in the scanning area in a controlled manner.

An option of 3D motion device is Cartesian 550, the movement is achieved by 3 electric motors perpendicular to each other.

One option of Cartesian 3D motion device 550, is formed by synchronized adaptation of two commercial bridge-type 3D printers 58 in a mirror configuration joined by a bridge-type joint of long screws and guide bars/rods 61 in the Z-axis direction, with one motor in forward and the other in reverse; the motion in the X, Y, vertical plane is realized in the respective axes with the motors 60 in forward and reverse rotation direction respectively controlled by encoder 59, stretcher platform 62 (FIG. 30).

An option of 3D motion device is cylindrical 570, this is formed by the synchronized movement of the stretcher 62 plus the radial and angular movement of the movement of the C-shaped supporting structure 400 by means of endless screws 63 and electric motors 64 fixed to a curved structure 65 that can rotate with respect to a double supporting ring 66 that is fixed to the external structure of the device. 75 FIG. 31

An option for a 3D Cartesian motion device is that it allows continuous movement in the scanning area, by means of step-by-step DC motors and an encoder for movement control (encoder).

An option for a 3D motion device is that it allows a movement to be made in the Cartesian system by moving only the stretcher and keeping the focus point fixed with respect to the structure.

A 3D motion device option is that it allows to perform a movement in the Cartesian system by moving the stretcher and moving the fixed focus point with respect to the structure.

One 3D motion device option is that it allows motion in the cylindrical coordinate system by moving the stretcher only in the Z-axis direction and the focus point can rotate angularly and move radially.

C. External Support Structure

The support structure is the external structure which allows the installation of all the parts and pieces of this invention and the shielding. One option of the support structure consists of a rigid arch 51 fixed to a metallic base 50, base with supporting legs 49, on which the scanning X-ray tube 12 and treatment tube 47 are fixed, as well as the entire 3D displacement device 550 of Cartesian type (X, Y, Z). FIG. 34. The complete Cartesian device is shown in FIG. 35.

One option for the support structure consists of a double circular ring 66 which can be fixed to the convergent scanning 100 and treating device 300, as well as the entire cylindrical type 3D displacement device with radial and angular coordinates (r, θ), the third component of the movement is achieved with a stretcher 62, which can be independent of this structure and moves only in the Z direction, FIG. 36. The complete cylindrical device is shown in FIG. 37.

D. An Electronic System and Control Method
  a. Programmable Electronic System 700 comprises five parts:
    1) One of them is the electronics associated with the detectors,
    2) another has to do with the control of convergent systems, whether they are dynamic or fixed,
    3) another device controls fast gate of treatment beam,
    4) another system is the laser guides of the confocal system.
    5) The other system is the one that controls the 3D motion device and corresponding transducer (encoders). See FIG. 38
  b. One method is applied by means of a computer 800 with a main software that enables and controls the operation of all the previous units and also the pre-established software of commercial units that may be part of some of the preferred options of this invention. Specifically allows to;
  i) Enable and control the electronic system corresponding to the motors that allow the movements associated with the convergent devices and those associated with the 3D scanning/sweeping movement,
  ii) Enable the operation of the detectors and control the acquisition parameters such as: recording mode, energy windows, acquisition time, time associated with the pulse, spectral gain, number of recording channels and others in the software.
  iii) Link the coordinates of the scan positions of the 3D motion device 500 with the recording of the fluorescent signals generated at each biomarked focal point, thus generating a 3D array of positions with fluorescent intensities.
  iv) Set the rotation speed of dynamic devices Establish the operating parameters: current, voltage, shot times associated with the X-ray tubes.
  vi) Establish automatic communication between detection and triggering based on the existence or not of a fluorescent signal associated with a point of the scanning matrix with the opening or closing of the treatment beam curtain, respectively.
  vii) Control the relative position of the focal points of dynamic or static convergent devices, using stepper motors with encoders.
  viii) Control the focal point of a dynamic converged device.
E. A computerized tomography CT (2000) consisting of: orthovoltage X-ray tube 77, a system of collimators 78, and detectors 79 is incorporated in the same structure 600.
  One CT option is by incorporating a ccd or flat panel plate, to record the signal transmitted by the X-ray tube that is used from the convergent beam of exploration and by means of reconstruction software, the anatomical 3D image can be obtained.
  Another faster CT option can be housed in the double ring structural rail 66 by using an X-ray tube 77 and a fast detection system 79, taking advantage of the spaces left by the main device (2000), the rotation of a semi-circumferential structure 83, on a carriage 81 and the advancement of the stretcher 62; by means of a reconstruction software, the anatomical 3D image can be obtained. (FIG. 39). Although a CT is an existing element that can be added to the main device of this invention, the compact option that includes a CT is the most complete and allows having everything in a single rotating structure, reducing the costs of a combined device, in addition to the fact that CT technology is already in the public domain, since more than 50 years have passed since its invention. End view 3000 of the device for human applications in FIG. 40.

Device Operation

The three fundamental elements of this invention are connected solidly/jointly by means of a supporting structure 400 in confocal mode, which is attached to a 3D motion structure 500 performing on the sample to be analyzed ("fantoma", animal, person) which is fixed to a stretcher 62. The scan is controlled by a computer 800 with software that in turn coordinates the reading of the fluorescent signals coming from the detection system with the position of the scan, each reading is associated with a spatial point of the scan area, which defines the pixel of the 3D image that is built as the scan evolves, thus building a 3D matrix of intensities and therefore a 3D image of the tumor that would be found within the scan area is reconstructed. So far we have the EDXRF imaging system.

For a theranostic application, a second convergent beam device 300 and of higher intensity than the scanning beam device 100 attached to the same supporting structure annihilates the neoplastic cells in its path at the same biomarked points excited by the first beam, the focal point of the second beam being confocal or offset by a few mm from the point already scanned by the first convergent scanning beam device 100. When the detection system does not detect a fluorescent signal, a fast-triggered metal plate 41 interrupts the convergent beam. This allows the beam to be applied only at the coordinates indicated by the device control software, that is, when fluorescent signal is detected due to the excitation of the biomarked cells.

In summary, we can say that a first convergent beam together with a detection system and software allow an image of the tumor to be reconstructed and then a second, more intense convergent beam allows the punctual annihilation of the neoplasm. It is necessary to point out that this invention could not work in cancer applications if the tumors are not biomarked with metallic nanoparticles, such as those indicated in Table 1. In this regard, there is abundant scientific literature that shows that neoplasms can be selectively marked by nanoparticles (Gd and Au) or solutions of heavy metal elements such as (Gd and others), thanks to the fact that these can adhere to antibodies and these to neoplastic cells.

The convergent beam device can produce deep fluorescent excitation in the matrix up to about 10 or more cm, whose peak energies are of the order of 100 keV. In short, the device presented here can detect X-rays of heavy elements of K, with minimum concentrations of up to about 100 ppm in the target.

DETAILED DESCRIPTION OF THE INVENTION

Figure 1:
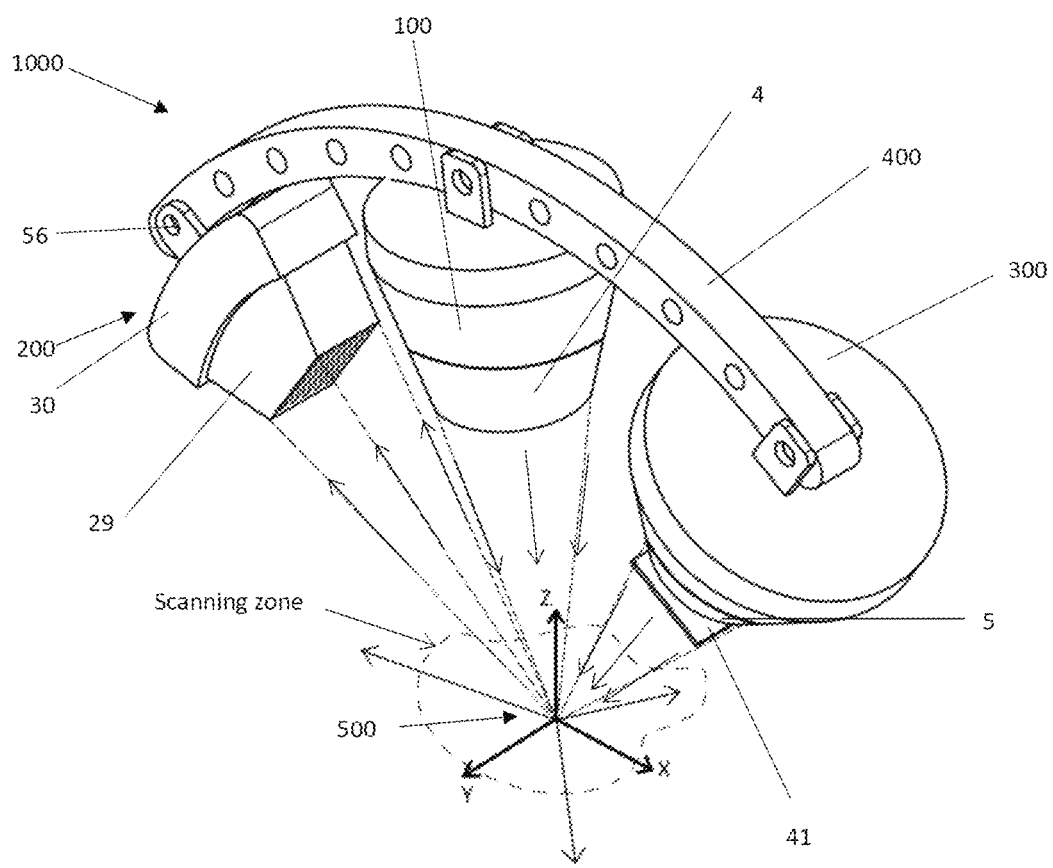
FIG. 1 basic device on support structure.

According to what is shown in at least FIGS. 1, 2, 3, 16, 19, 21, 26, 31, 32, 38 and 39, the present invention discloses a system for detecting, obtaining images and treating or eliminating neoplasms, pathologies or other anomalies, which is excited through X-rays biomarked with metallic nanoparticles comprising:

An external shielded support structure 600 comprising:

A. a confocal system (1000) comprising a shielded external structure (67, 75), which inside comprises: a scanning X-ray convergent device (100), a detection system (200) for X photons with collimators solidary and confocal to the first device, a second convergent processing device (300) solidary to the same confocal structure (100 and 200) and a supporting structure (400) containing the scanning X-ray convergent device (100), the detection system (200) and the second convergent processing device (300), which project to a single focal point and which ensures that they are confocal;

B. a controlled 3D scanning structure (500) moving a stretcher and/or focal point where the ionizing radiation is concentrated;

C. an electronic control system comprising:
a programmable electronics (700) allowing the operation of the convergent beam device, the operation of the detectors (2) and the movements of the 3D scanning system; and D. a computerized tomography CT (2000) comprising collimators, X-ray tube and detectors is incorporated in the same structure (600).

Which also includes a large confocal system (1000) of at least 100 cm$^3$ or more disposed of three essential elements (100, 200, 300) (FIG. 1).

Figure 2:
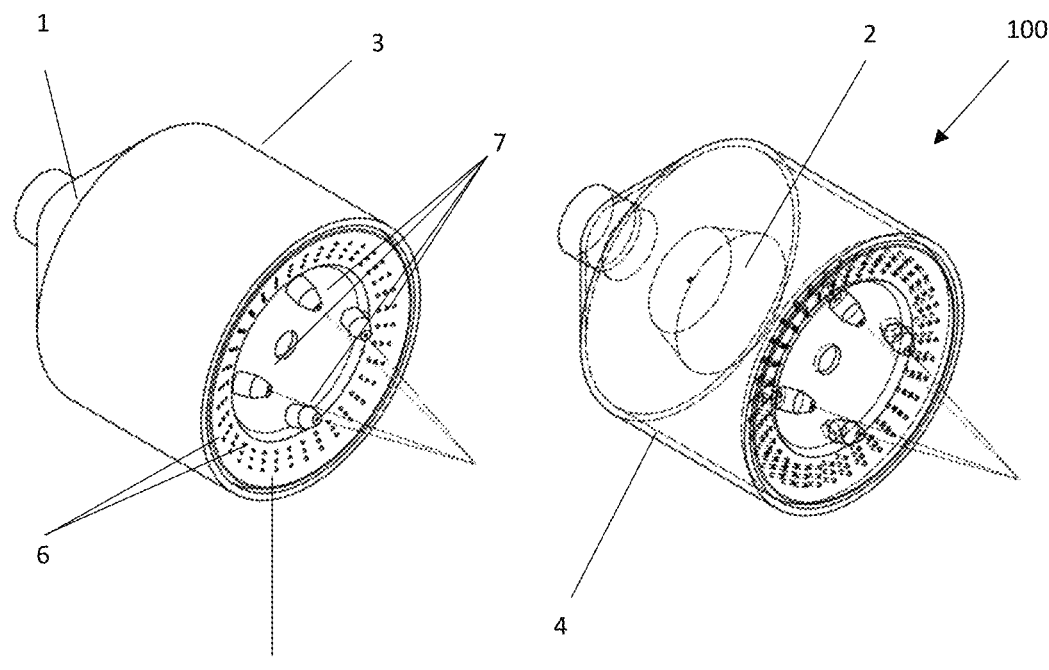
FIG. 2 large convergent beam cylindrical X-ray tube formed by a curved cylinder as the anode.

In a preferred configuration, it has a static cylindrical convergent ionizing radiation scanning device (100) in vacuum, consisting of an electron gun (1), a beam braker (2), a white metallic cylinder 3 of high Z (>50) covered by a cylinder of a conductive material (Al or Cu) (4), a spherical cap (5) as collimator with separate collimation holes 6 pointing to a focal point and confocal laser guides (7) (FIG. 2).

Figure 3:
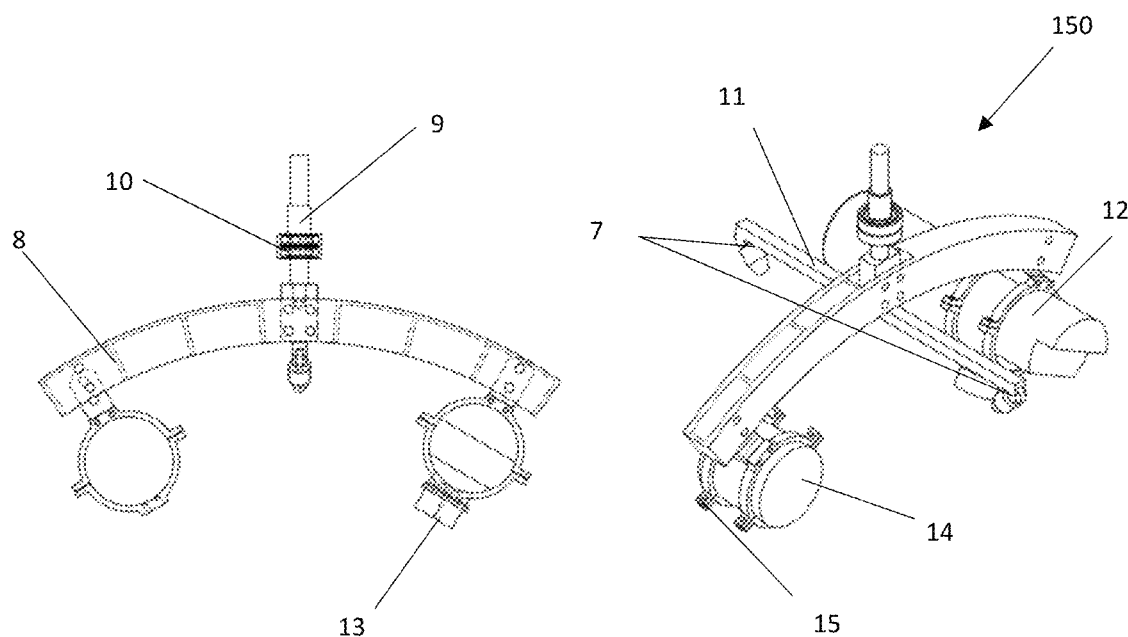
FIG. 3 shows elementary dynamic convergent device with support arm and rotation shaft/axis.

In another preferred configuration it has a dynamic convergent ionizing radiation scanning device (150), formed by a rotating arc support (8) with shaft/axis (9), bearings (10), bar (11) with confocal laser guides (7), X-ray tube (12), collimator (13) and counterweight (14) at one end, rotating by means of a reduction and connection system (53) and an electric motor (52), collimator (13) and counterweight (14) at one end, rotating by means of a reduction and connection system (53) and an electric motor (52), the X-ray output is collimated by means of a collimator 13 that points to the focal point of the system 150 (FIG. 3).

Figure 4:
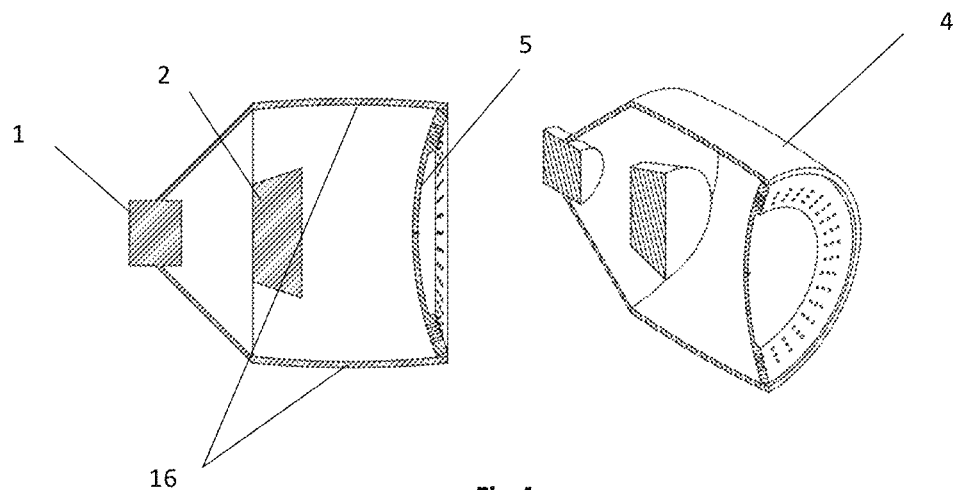
FIG. 4 shows a convergent beam device formed by a curved cylinder.
Figure 5:
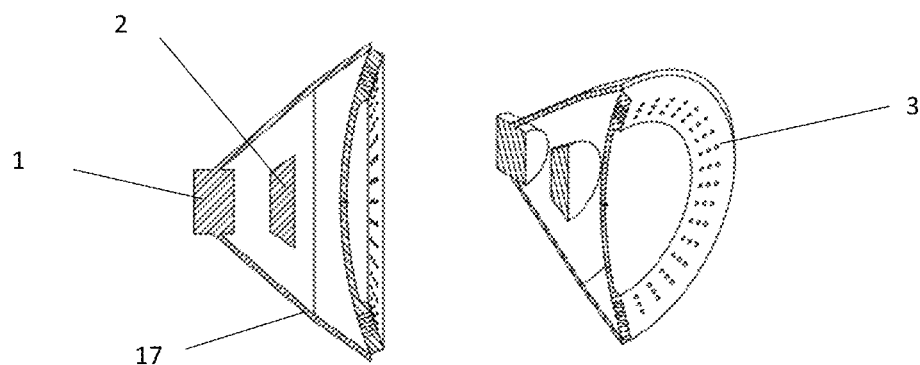
FIG. 5 shows a convergent beam device formed by a curved ring as the anode.
Figure 6:
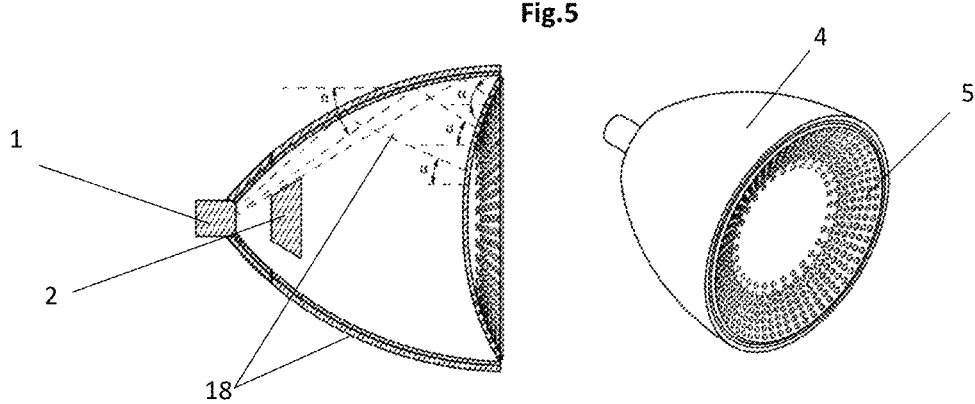
FIG. 6 shows convergent beam device formed by long curved cylinder as anode.

Where, the device is formed by a curved anode cylinder (110) (FIG. 4) or a curved anode ring (120) (FIG. 5) or by a long curved anode cylinder (130) (FIG. 6).

Figure 7:
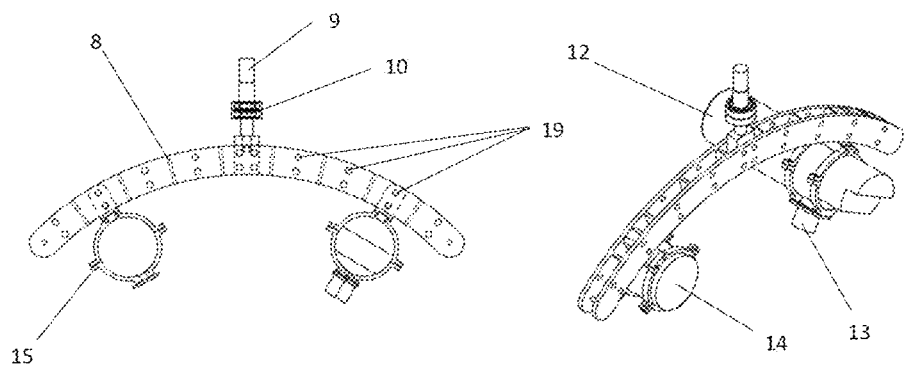
FIG. 7 shows dynamic convergent device with curved support arm, with shaft of rotation and fixed holes in different positions.
Figure 8:
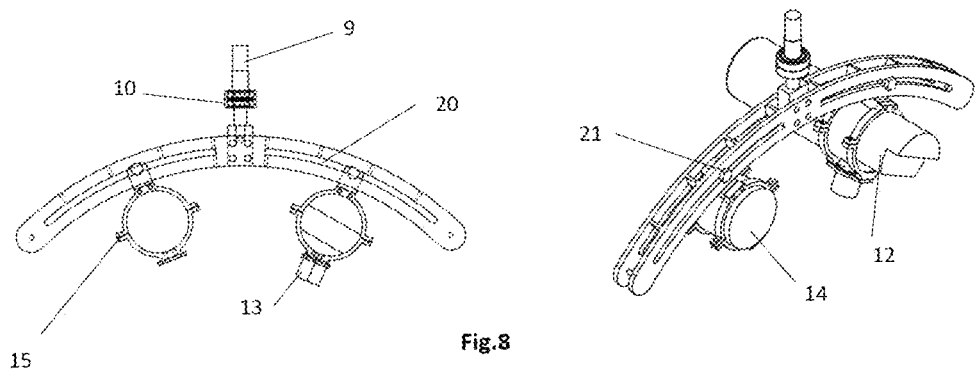
FIG. 8 shows a dynamic convergent device with a curved support arm C, shaft of rotation and slots that allow the angle of the convergent cone to be set.

In another preferred configuration, it has a support structure (8, 24) with position adjustment means (19, 20, 22, 27) that allow the X-ray tube (12) to be fixed with the direction of its collimated output pointing towards the focal point and its projection is perpendicular to the tangent line of the arc that intersects it, the convergent cone angle is generated at preset positions without changing the position of the focal point (FIGS. 7 a 13).

In another preferred configuration, the support structure is selected from a supporting arch (8) or a straight arm (24) centered at the focal point.

In another preferred configuration, the position adjustment means are selected from among position holes (19), a long curved slot (20), a curved toothed slot (22) or a straight toothed slot (27) that allows varying the convergent cone angle.

Figure 9:
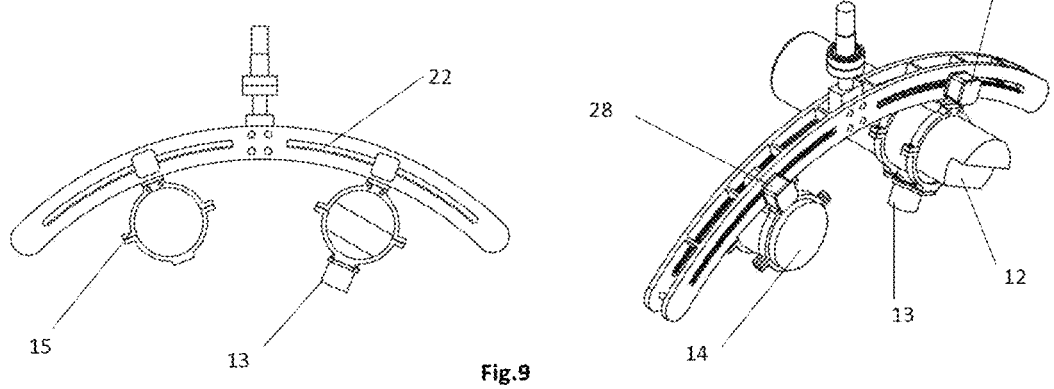
FIG. 9 shows a dynamic convergent device with a curved supporting arm, with a shaft of rotation, with slots along it, with racks and motors.

The system also comprises an electric motor (23) that allows the angle of the convergent cone to be varied continuously, and two other motors (23) moving the X-ray tube 12 together with the counterweight 14 in opposite directions along the C-arc respectively (FIG. 9).

Figure 10:
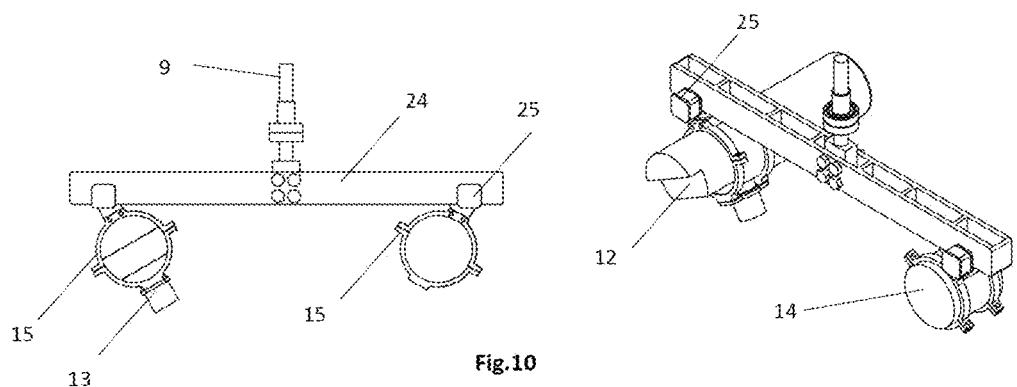
FIG. 10 shows a straight arm dynamic convergent device with a rotation shaft, with a fixed radius and angle.
Figure 11:
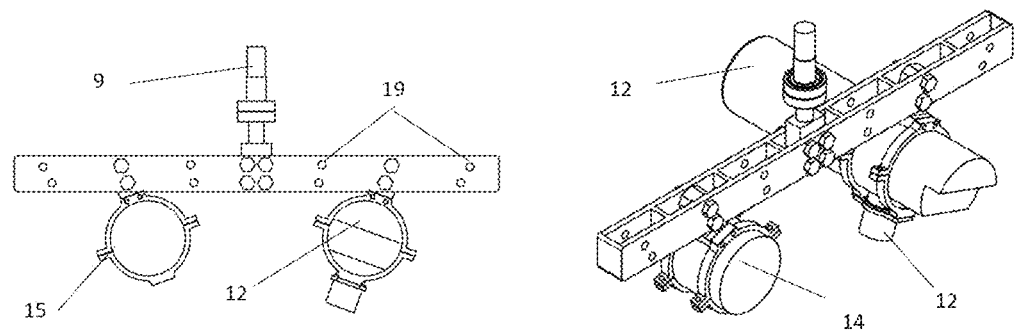
FIG. 11 shows dynamic convergent device with straight arm with rotation shaft, with holes fixed in different positions, same focal point.
Figure 12:
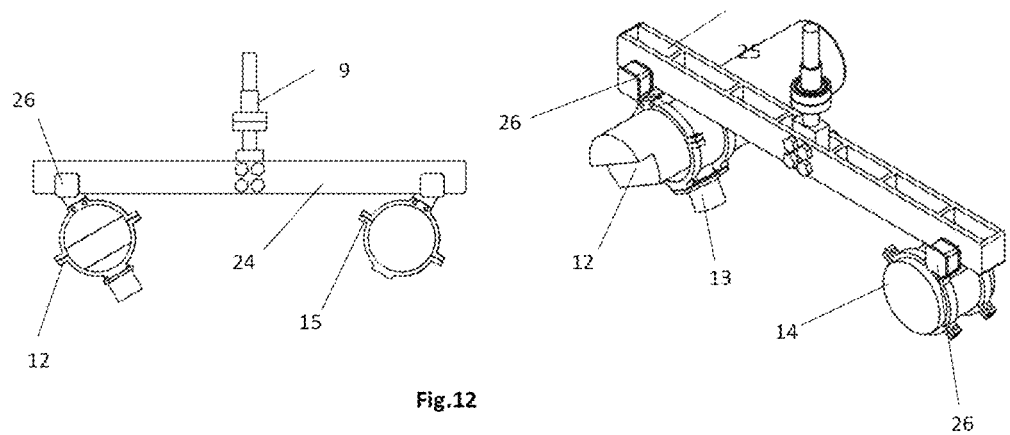
FIG. 12 shows dynamic convergent device with straight arm with rotation shaft, with motors to vary the angle of the X-ray tube and counterweight.

Wherein, the support structure comprises an angular fixing (25) and an angular electric motor (26) to vary the angle of the convergent cone (FIG. 10, 12).

Figure 13:
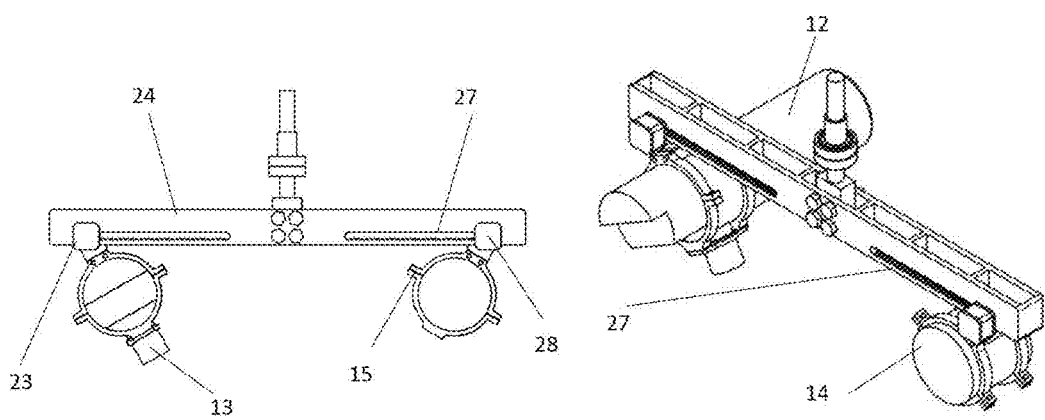
FIG. 13 shows a dynamic convergent device with a straight arm with a rotation shaft, with a long slot with a rack and electric motors.

In another preferred configuration, the support structure is attached to the system by means of the shaft (9), straight arm 24 and has straight toothed slot (27) along the arm with shaft 9 and an electric motor that allows to vary the angle of the convergent cone (28) in a continuous way, and two other motors (23) move the X-ray tube together and the compensator in opposite directions along the arm respectively (FIG. 13).

Figure 14:
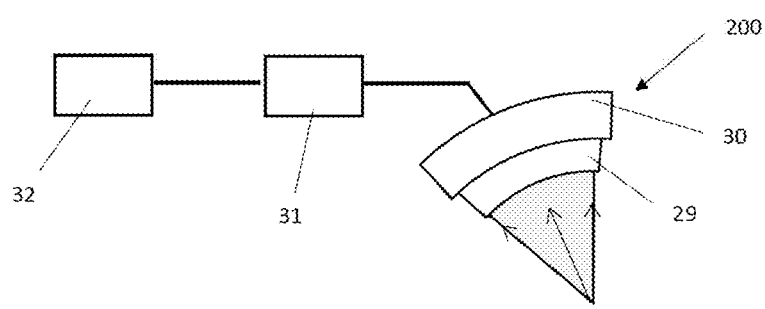
FIG. 14 shows a schematic of the confocal detection system.

Wherein, a confocal detection system (200), formed by a collimator with one or more confocal septa (29) attached to the input of the X-ray detector (30) with energy resolution in, followed by an amplification system (31) and MCA multichannel pulse processing (32) (FIG. 14).

Figure 15:
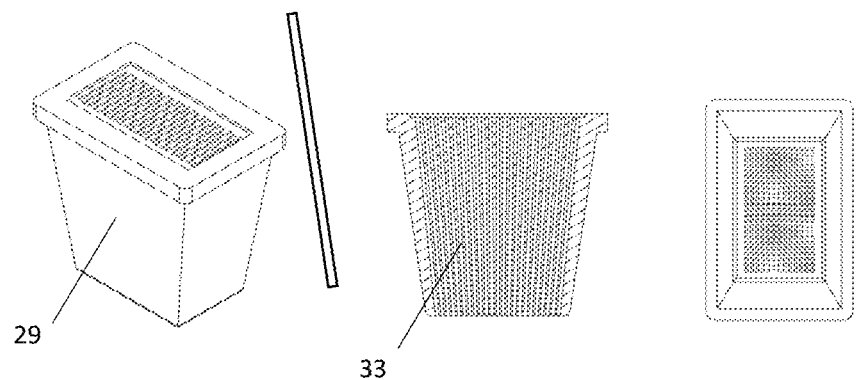
FIG. 15 shows a large-area confocal collimator with straight confocal septa.
Figure 16:
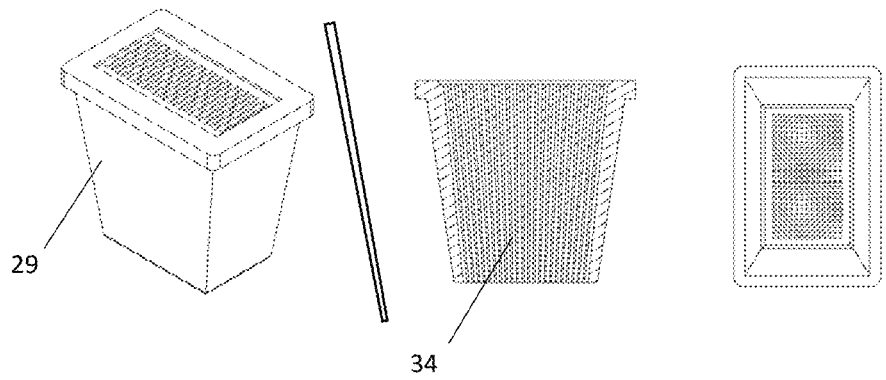
FIG. 16 shows a large-area confocal collimator with conical confocal septa.
Figure 17:
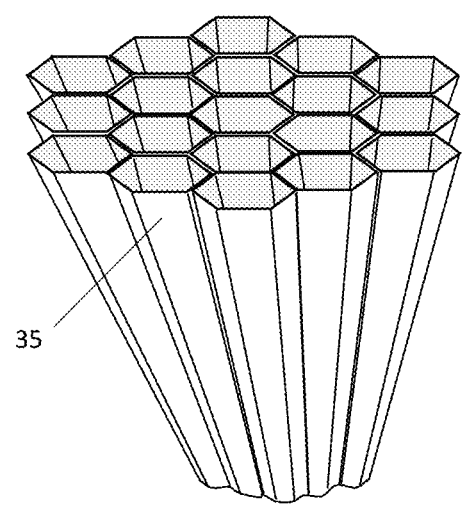
FIG. 17 shows large-area confocal collimator hexagonal honeycomb confocal septa.

In another preferred configuration, the detector collimator (30) has one or more straight cylindrical (33) or conical (34) septa or hexagonal conical honeycomb-shaped septa (35) (FIG. 17), (FIG. 16) (FIG. 15).

Figure 18:
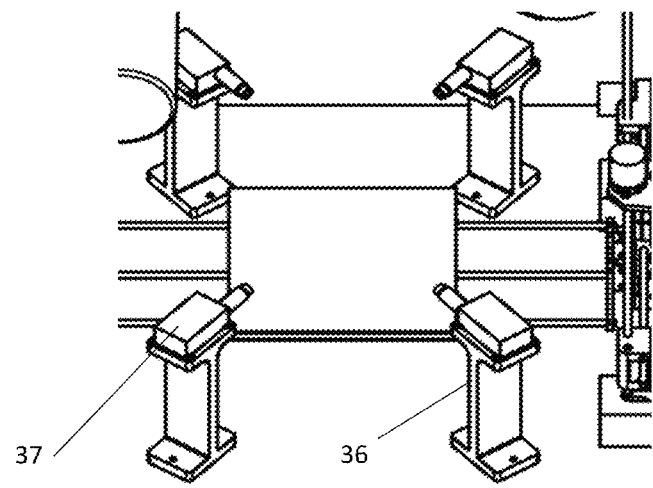
FIG. 18 shows a detection system formed by a set of solid state detectors of the CdTe type.
Figure 19:
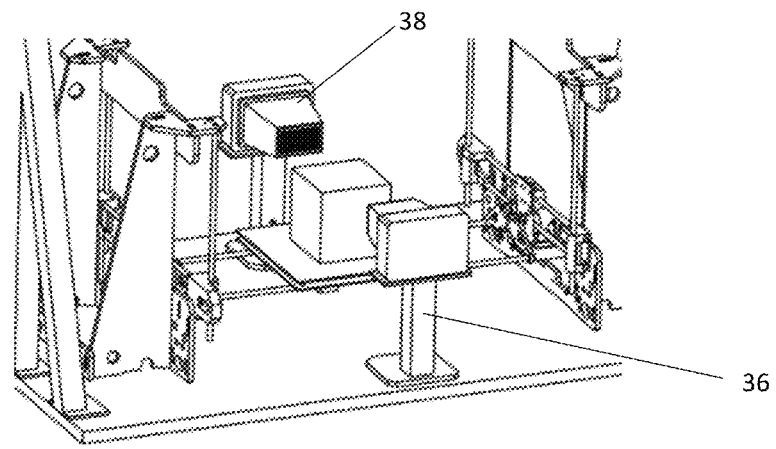
FIG. 19 shows detection system with two confocal detectors with larger detection area ~100 cm$^2$ each.

Wherein, the detector system consists of one or more solid state detectors, which are chosen from cadmium telluride (CdTe) (37) on support (36) or hyper pure Germanium (Ge) or NaI(Tl) sodium iodide scintillator. (FIG. 18).

In another preferred configuration, the detector system (30) is made up of at least one or more confocal detectors with an area greater than $0.25^2$ cm$^2$) (38). (FIG. 18).

Figure 20:
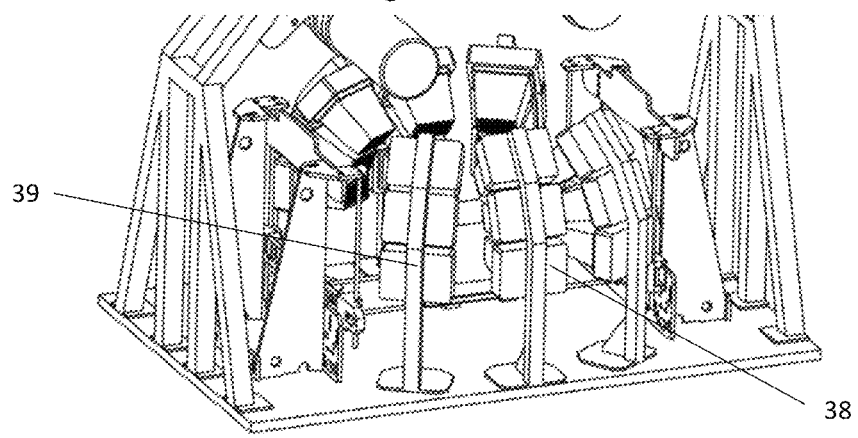
FIG. 20 shows a detection system with a greater number of confocal detectors with a larger area.

The detector system (30) is made up of at least two area confocal detectors (greater than 0.25 cm$^2$) (38), configured concentrically, until covering the entire visible radiation output area of the object to be analyzed isotropically (FIG. 20).

The second convergent treatment device (300) has higher power than the convergent X-ray scanning device (100), wherein the second convergent treatment device (300) comprises direct electrical contacts and included cooling systems.

Figure 21:
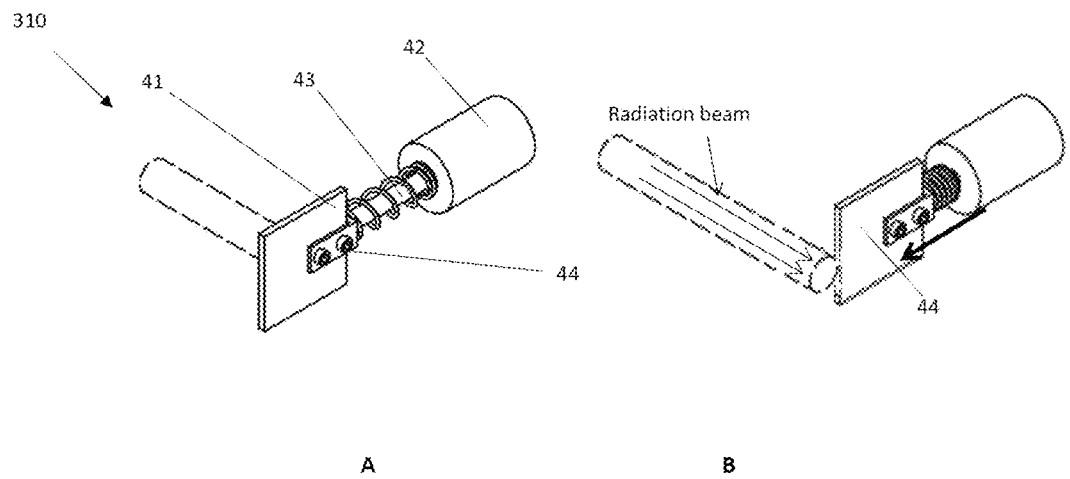
FIG. 21 shows a fast beam attenuator gate formed by a metal foil driven by a solenoid.
Figure 22:
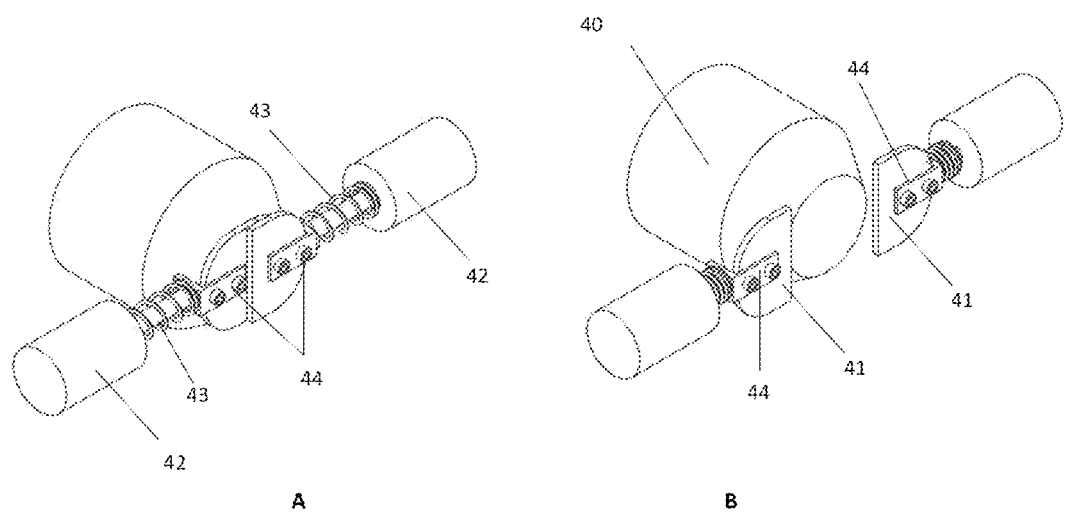
FIG. 22 shows a fast double gate for complete attenuation (<1%) of the static convergent beam formed by metal foils driven by a solenoid.

In another preferred configuration, a fast gate (310) comprising at least one metal foil (41) attached to a bidirectional solenoid (42) which moves the foil to output the beam only when there is a fluorescent signal recorded by the detection system, wherein at least one metal foil (41) is permanently interrupting the beam, to completely attenuate the beam (<1%), when no fluorescent signal is recorded (FIGS. 21 and 22).

Figure 23:
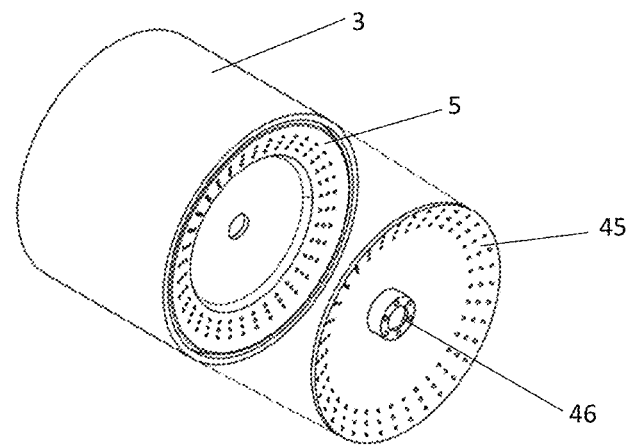
FIG. 23 shows a spherical circular gate for full attenuation (<1%) with holes following the same hole pattern as the collimator, with axis on the optical axis of the static convergent device.
Figure 24:
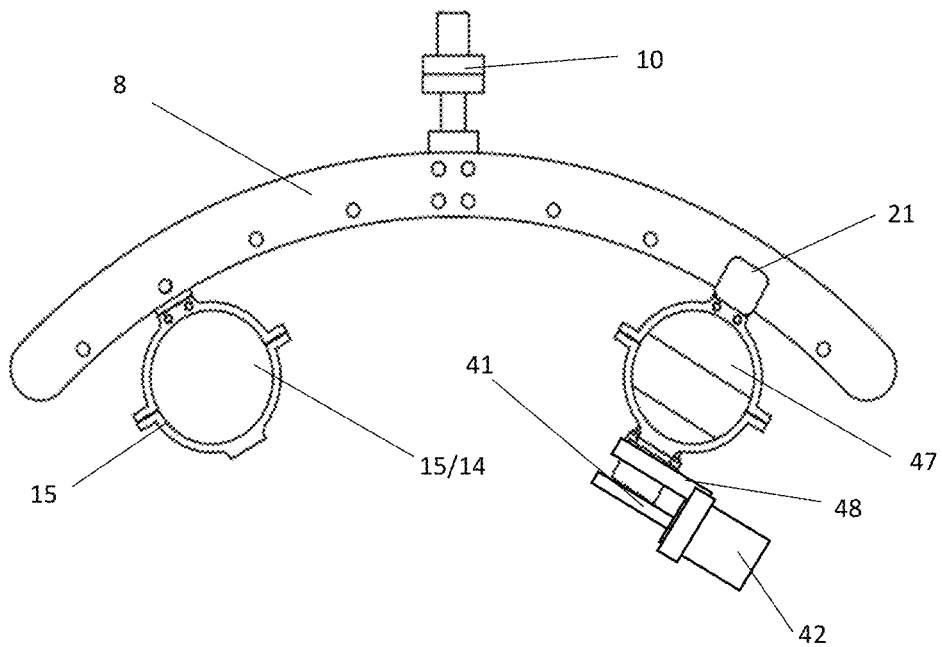
FIG. 24 shows a fast gate for complete attenuation (<1%) of the dynamic convergent beam formed by a metal foil driven by a solenoid, mounted on the collimator output.
Figure 25:
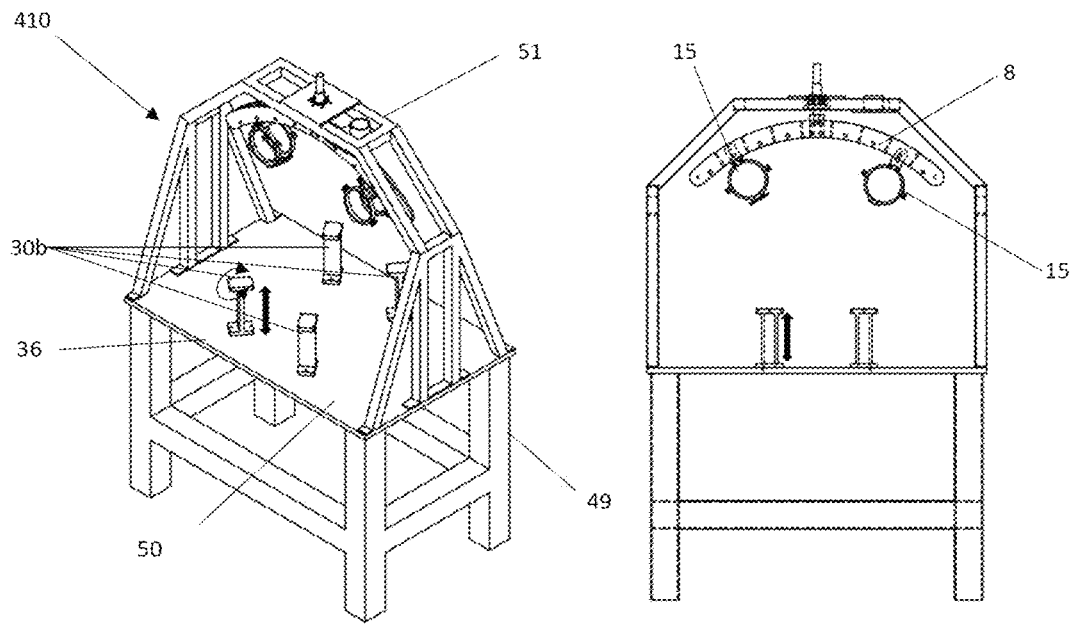
FIG. 25 shows the supporting structure for the Cartesian movement option, it is formed by an arch where the convergent sources are supported and the base for the support of the detectors.
Figure 26:
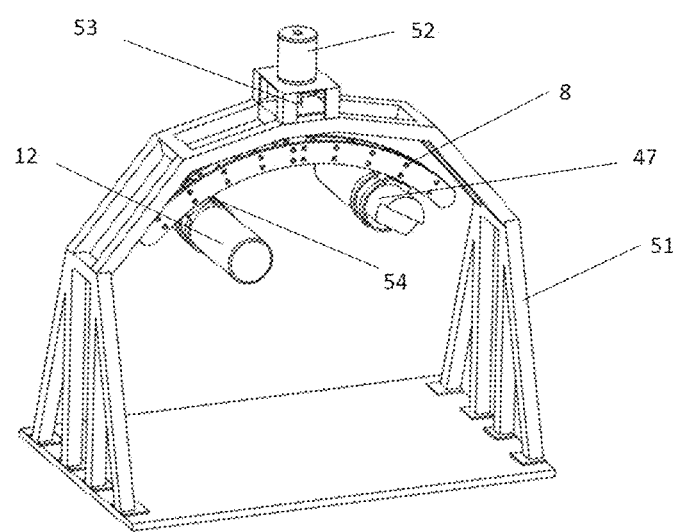
FIG. 26 shows Cartesian support structure with two convergent dynamic scanning and processing devices.
Figure 27:
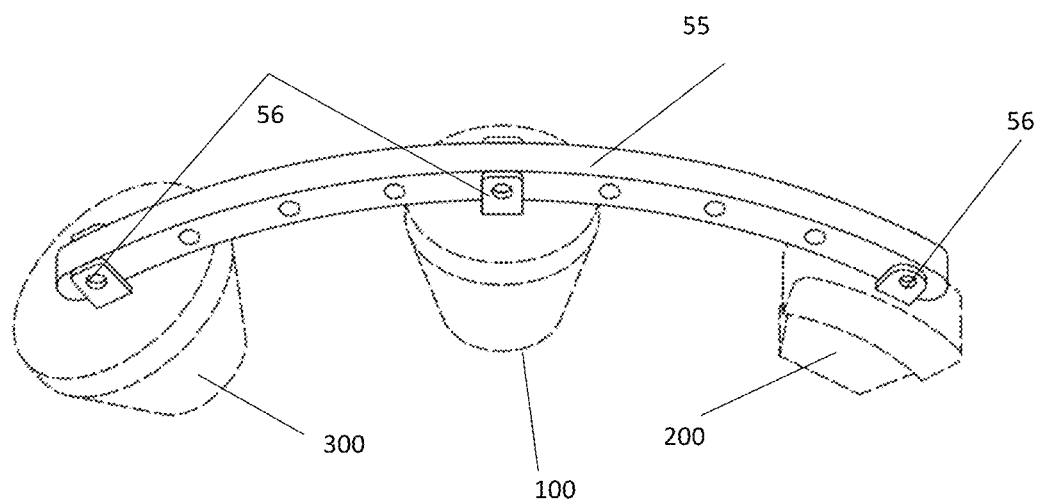
FIG. 27 shows a supporting structure with cylindrical movement, formed by a C-shaped arch on which the three basic devices are supported.
Figure 28:
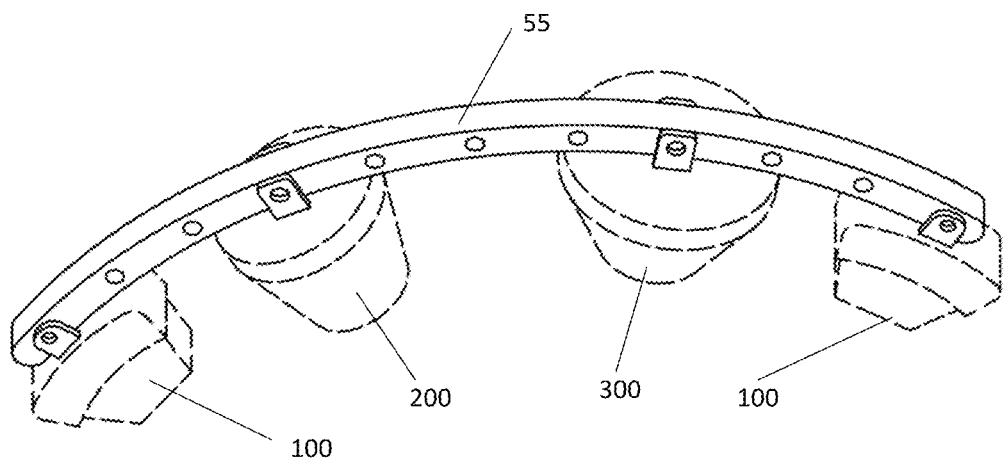
FIG. 28 shows the supporting structure of cylindrical movement, formed by a longer C-shaped arch with an additional detector.
Figure 29:
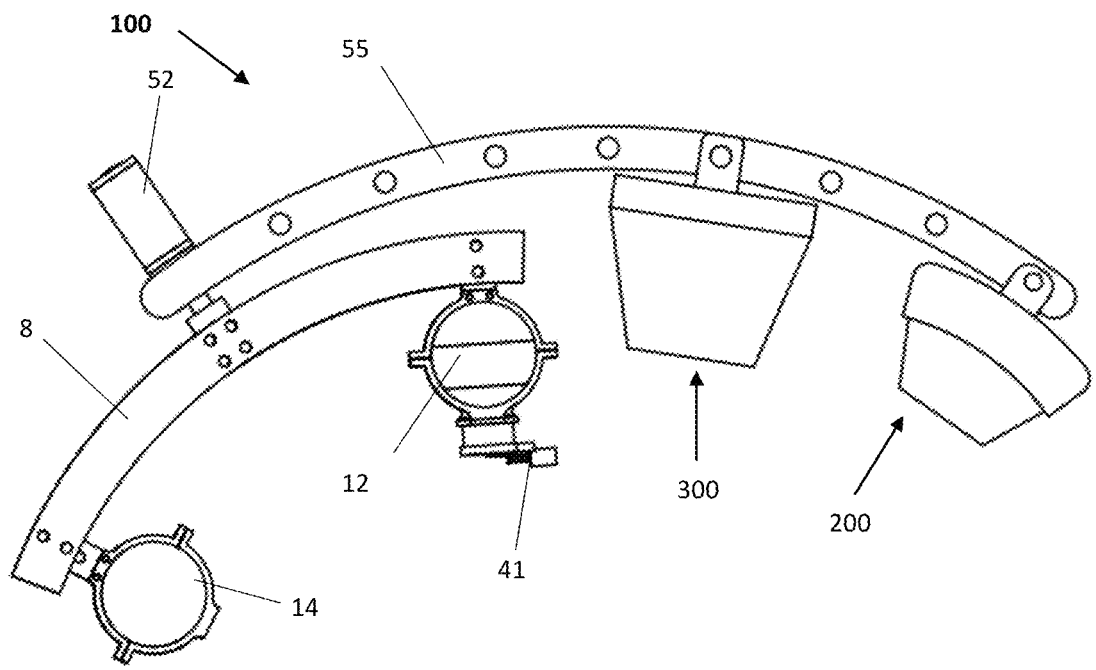
FIG. 29 shows the supporting structure of cylindrical movement, formed by a C-shaped arch with a combination of static dynamic convergent elements.

The static convergent scanning convergent device (100) or fixed convergent treatment device (300) comprises a circular spherical hole gate (45) comprising the same plurality of holes and with the same hole pattern as the spherical poly collimator (5), wherein the circular spherical gate with holes (45) rotates angularly and concentrically to the axis of the static scanning convergent device (100) or fixed treatment convergent device (300), to open the passage of the radiation beams, through a stepper motor (46), as it is permanently closed when the unit (200) does not detect fluorescent signal. (FIG. 23).

Wherein, the support structure for Cartesian scanning (410), is formed by a flat base with grip holes (36) for support of detectors (30*b*) and the structure (51) comprising the rotating arc support (8), which on its opposite sides has the supports for the X-ray device (12) to generate the convergent scanning beam 150 and the supports for the X-ray tube (47) to generate the beam of the dynamic convergent treatment X-ray device (47), wherein the collimator at the exit of the X-ray tube of the rotating device is mounted on a base that allows micro displacements in the X, Y plane.

In another preferred configuration, the Cartesian support structure (410) further houses Convergent Scanning Device (100) and Convergent Treatment Device (300) in a combination of static and/or dynamic devices.

Wherein, the 3D Cartesian displacement structure (550) of the stretcher (62), comprises a set of rails (61) for linear displacement (X, Y) and another set of rails (61) for vertical displacement, through driving means (59, 60), to perform the Cartesian movement (X, Y, Z)

Figure 30:
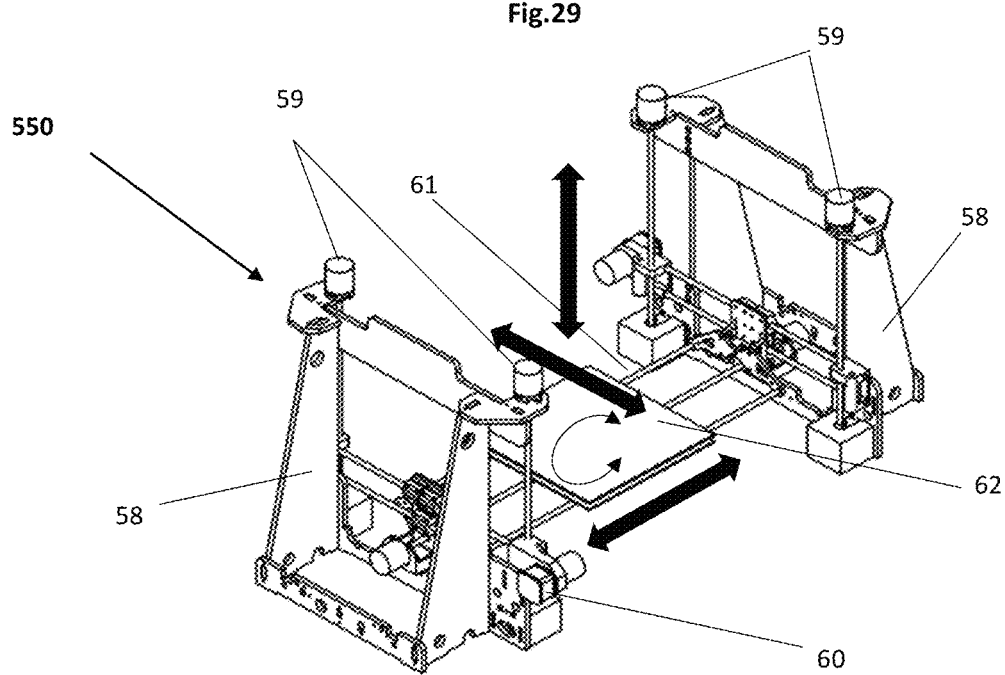
FIG. 30 shows the 3D Cartesian motion device, formed by the synchronized adaptation of two commercial 3D bridge-type printers in a mirror configuration that gives the system more robustness.

Wherein, the 3D Cartesian polar Cartesian displacement structure (570) of the stretcher (62), comprises a set of rails (61) for linear displacement (X) and another set of rails (61) for vertical displacement (Z), through driving means (59, 60), and a means for angular displacements of the stretcher (62). (FIG. 30).

Figure 31:
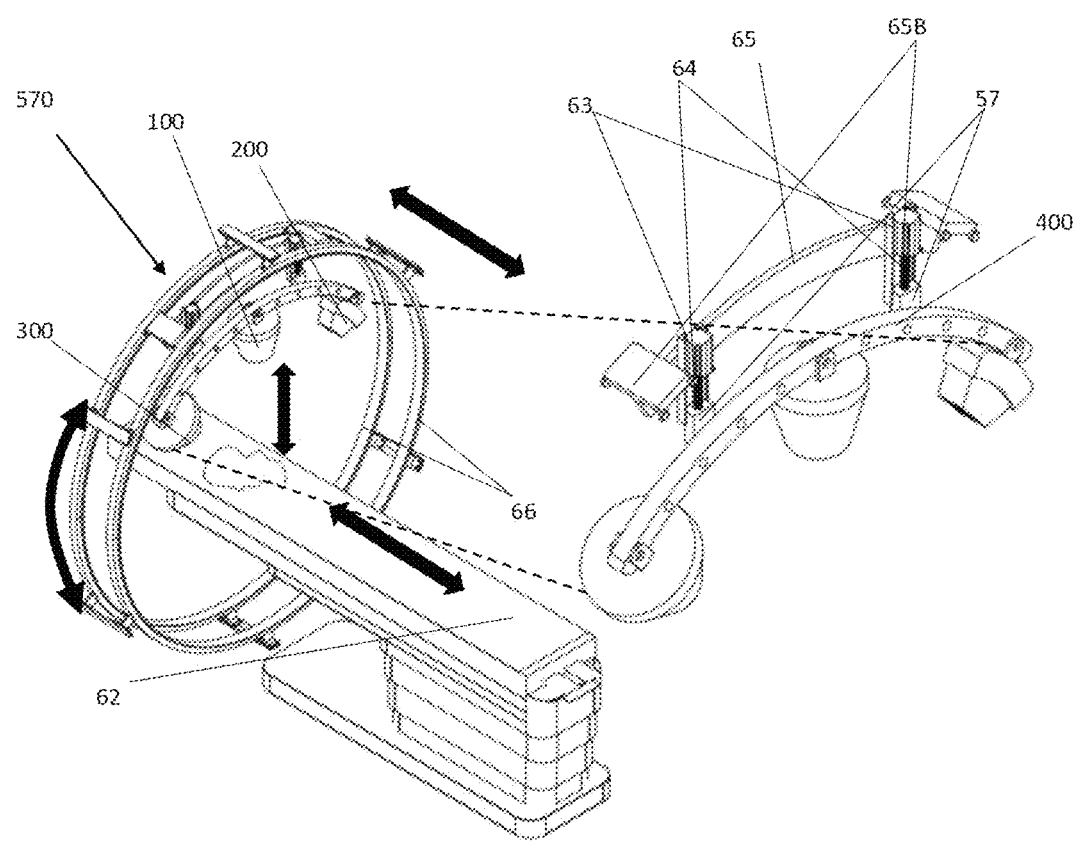
FIG. 31 shows a cylindrical 3D motion device, formed by the synchronized movement of the stretcher in the Z axis plus the radial and angular movement of the movement of the C-shaped supporting structure.
Figure 32:
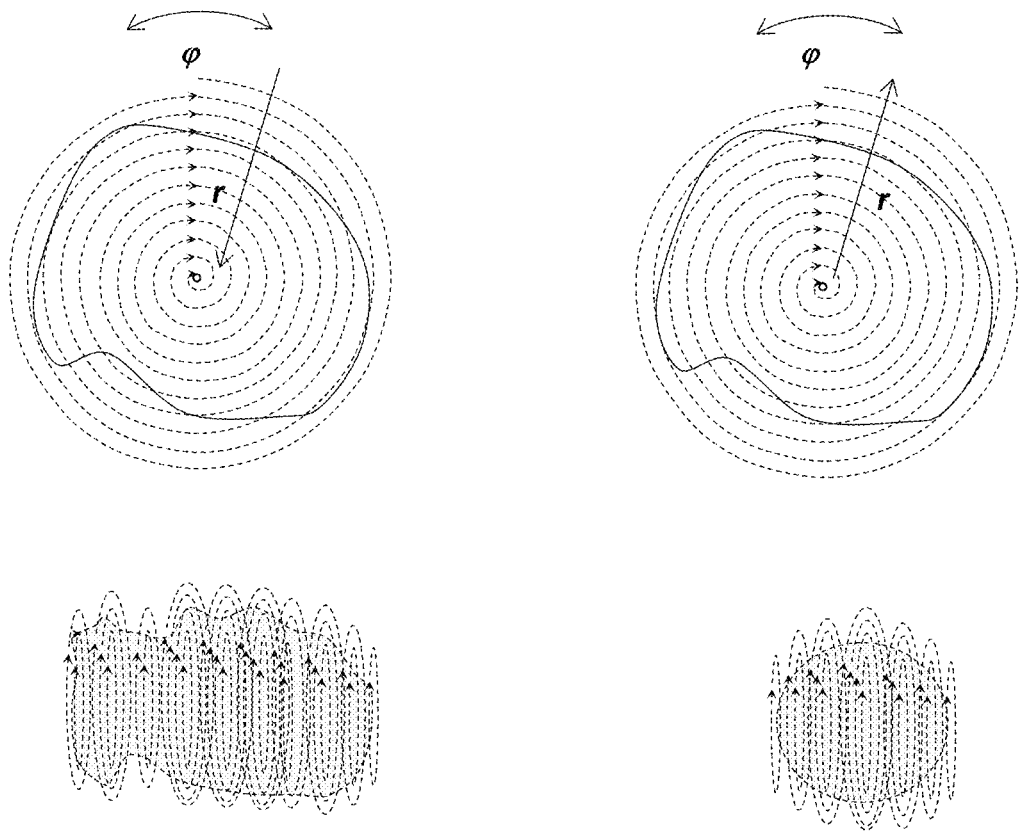
FIG. 32 shows cylindrical scanning/sweep scheme.

Wherein, the supporting structure (400) further comprises sliding guides along the arc (not shown in the figures) for moving the fixed convergent treatment device (200) the fixed convergent treatment device (300) and/or the static convergent scanning device (100) (FIG. 31).

In another preferred configuration, a shielded external structure (67) that is mounted above the Cartesian support structure (410), wherein the shielded external structure (67) comprises shielded door (68).

Figure 35:
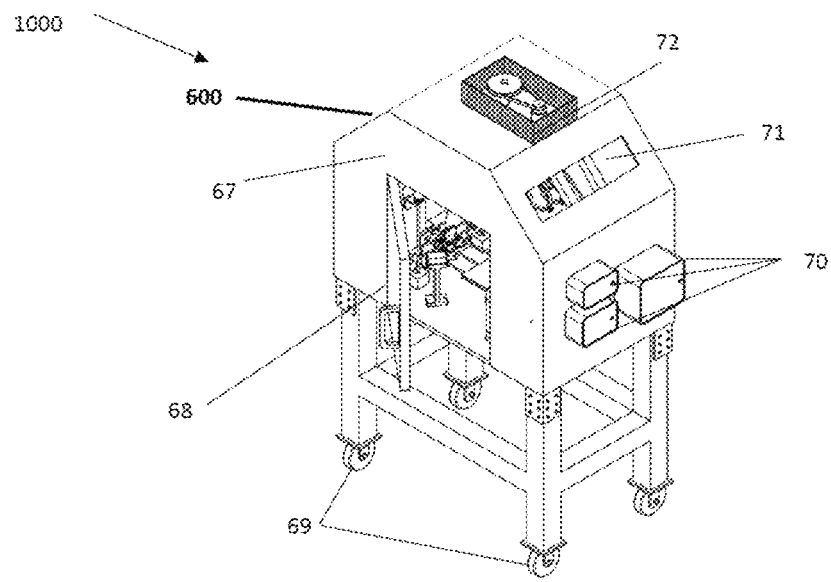
FIG. 35 shows closed, complete Cartesian external support structure.
Figure 36:
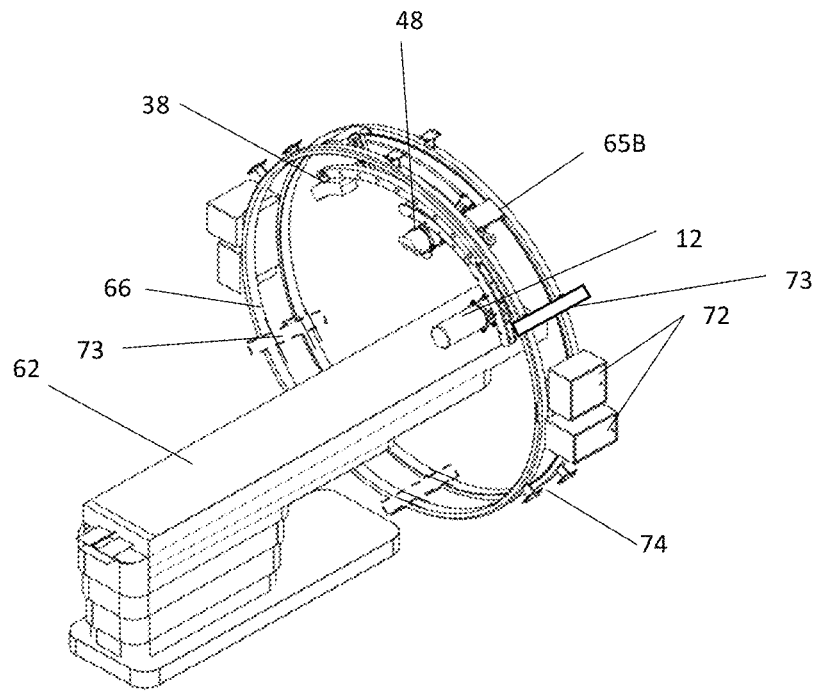
FIG. 36 shows a cylindrical external support structure that allows the installation of all the pieces and essential parts of this invention and the shielding.
Figure 37:
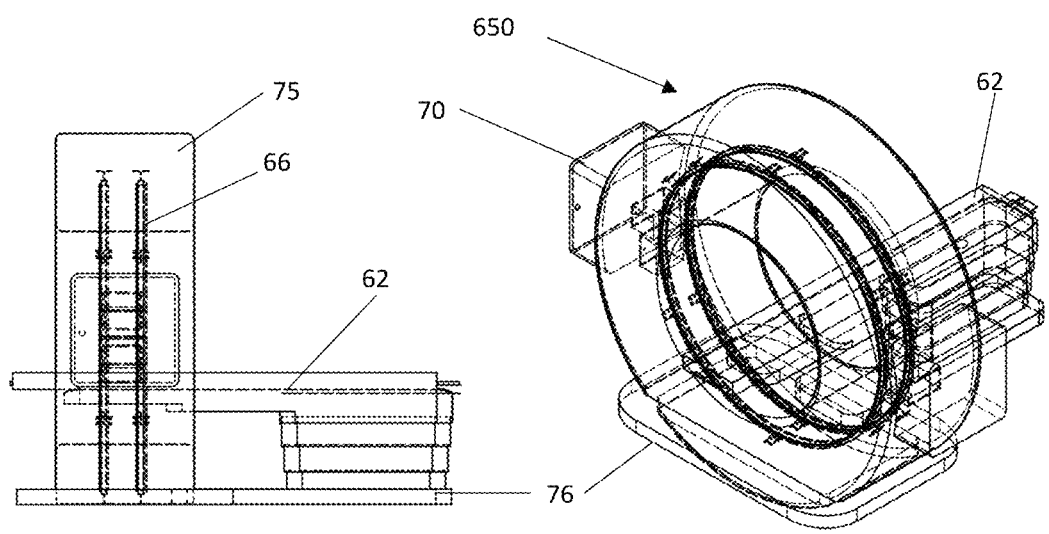
FIG. 37 shows closed, complete Cartesian cylindrical external support structure.

Wherein, the external shielded structure (67) comprises, a shielded observation window 71 and/or a set of cameras, some electronic control elements 70. (FIG. 35).

In another preferred configuration, its cylindrical polar version comprises a double ring structural rail (66) with connecting plates (73), which supports a curved structure (65) with carriages (65*b*), which is joined by means of parallel guides with screws (64) to the supporting structure (400) by means of two parallel joints with wire (57) and motors (63), in turn, the double ring structural rail (66) is joined to an external cylindrical structure with shielding (75) and central hollow, which in its external part houses external boxes for electronic control elements (70), on a support base (76); a stretcher (62) is located along the axis of the structure (75); this whole assembly (75, 62) allows movements of the supporting structure 400 in radial (p) angular ((p) and longitudinal (z) direction.

Figure 38:
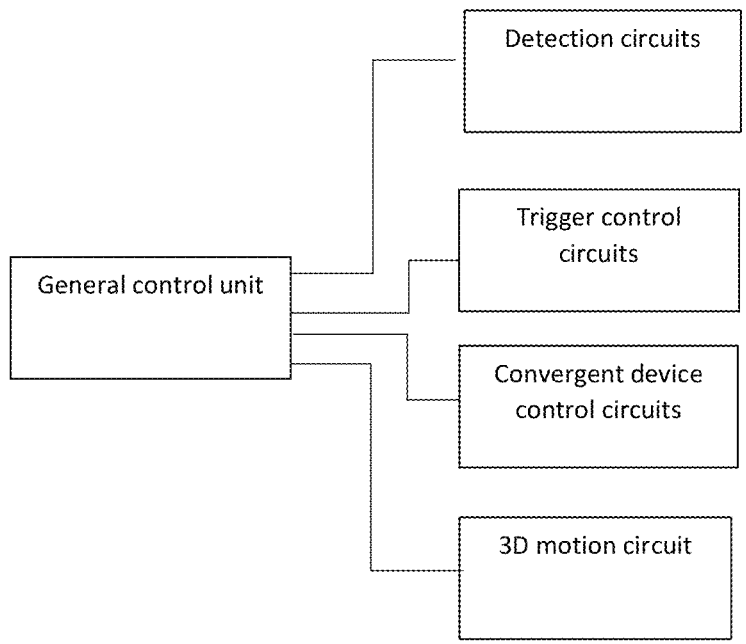
FIG. 38 shows the overall schematic of the electronic circuit with electronic circuit box associated with the five electronic circuit units that make up the complete system.

The detection system, comprising a general control unit which is connected to: a detector circuit controlling the detectors (200), wherein the detectors are mounted on a base allowing angular and Cartesian micro displacements; a trigger control circuit, for controlling the at least one bidirectional solenoid (42) and letting the processing beam through; convergent device control circuits, for controlling the convergent devices (100, 150); and 3D motion circuitry, for controlling the motors (59, 60), wherein said circuits are controlled by a central processing and communication unit (FIG. 38).

Figure 39:
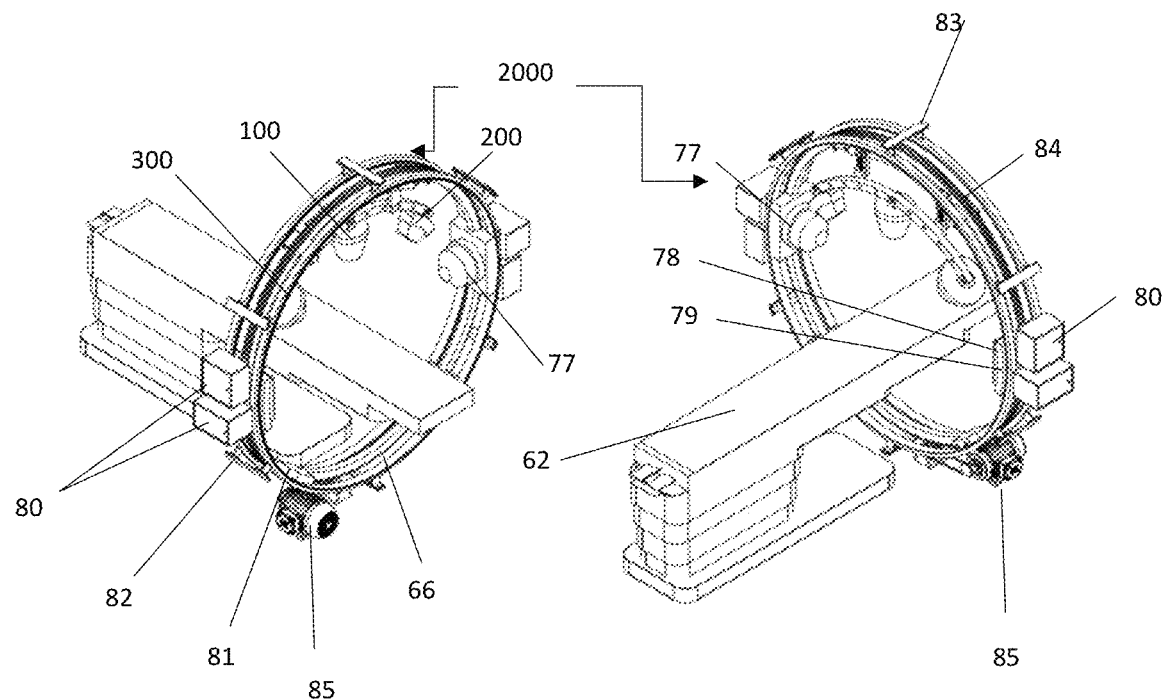
FIG. 39 shows global structure with incorporated CT (Scanner or Computerized Tomography)
Figure 40:
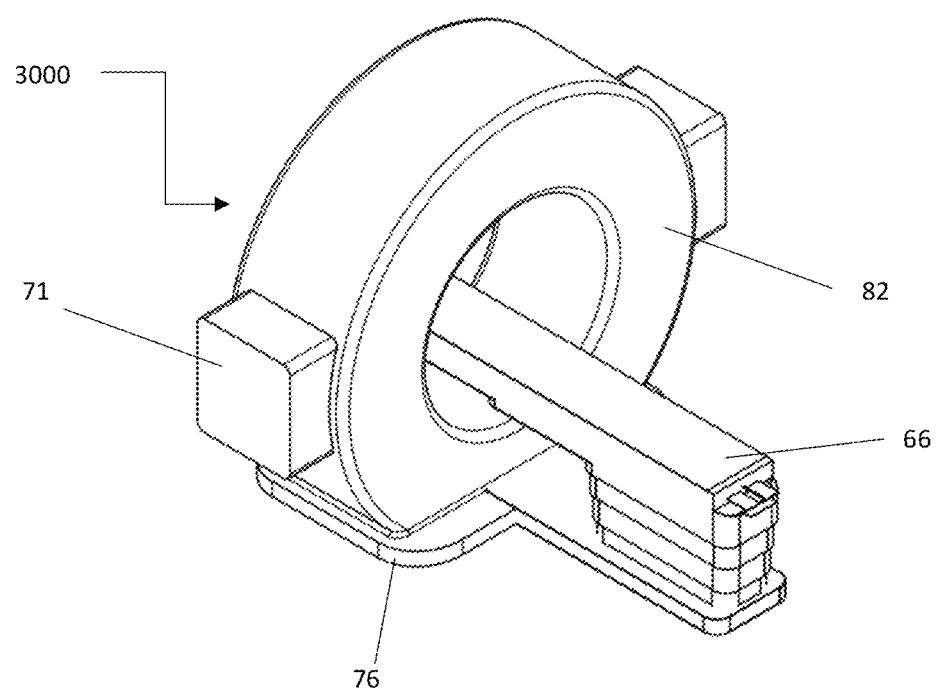
FIG. 40 shows: complete view device closed.

In another preferred configuration, it further comprises a computed tomograph (2000) comprising: a conventional X-ray tube (77), a system of collimators (78) and detectors (79) within the fluorescent confocal system (1000), wherein the fluorescent confocal (1000) and the computed tomograph (2000) are within the shielding (75) which are connected by means of a ring guide support (83) to the double ring structural rail (66), wherein the shielding (75) is solidly attached to a base (76) (FIG. 39).

In another preferred configuration, the ring guide support (83) joins the shield (75) solidly with the double rail structural ring (66).

In another preferred configuration, the ring guide support (83) movably joins the shielding (75) with respect to the double ring structural rail (66), allowing the latter to rotate by 360°, in a controlled manner, the fluorescent confocal (1000) and the computed tomograph (2000).

In another preferred configuration, the X-ray devices (100) use energies in the orthovoltage range (100-750 keV).

Wherein, X-ray devices (100) use energies in the soft X-ray range, less than 100 keV, for surface applications.

In another preferred configuration, the convergent device (100, 150) has a dual function, first it operates in scan mode by marking the zone with a power of at least 50 W and second it operates in therapy mode by increasing the operating current with a power of at least 100 W.

Wherein, the focal point of the convergent scanning device (100) is advanced in its scanning path, with respect to the path of the second treatment device (300), wherein the second treatment device (300) have the same scanning path as the convergent scanning device (100) enabling the theranostic mode. (Simultaneous Diagnosis and Treatment).

In another preferred configuration, the offset between the focal point of the convergent scanning device (100) is at least 1 millimeter with respect to the second treatment device (300), enabling the theranostic mode. (Simultaneous Diagnosis and Treatment).

A method for detecting, imaging, and treating or eliminating neoplasms, pathologies, or other abnormalities, which is excited through X-rays biomarked with metallic nanoparticles comprising the steps of:
  A. capturing anatomical images of the individual ("fantoma", animal, person) to detect any anomaly, by means of a CT scanner (2000) which is inside an external support structure 600;
  B. if any anomaly is detected, then: mark an area of the individual and analyze the area with biomarker means through a confocal system (1000) by means of a three-dimensional scanning of the marked area, wherein the confocal system (1000) comprising an external shielded structure (67, 75), which inside comprises: an X-ray scanning convergent device (100), a detection system (200) for X photons with solidary collimators and confocal to the first device, a second convergent processing device (300) solidary to the same confocal structure (100 and 200) and a supporting structure (400) containing the X-ray scanning convergent device (100), the detection system (200) and the second convergent processing device (300), which project to a single focal point and which ensures that they are confocal; and
  C. if biomarker X-ray fluorescence signal is detected by detection system (200), then apply convergent treatment device (300), wherein convergent treatment device (300) applies radiation at the three-dimensional coordinates that the scanning X-ray convergent device (100) generated X-ray fluorescence detected by detection system (200).

In addition, it includes repeating step C, until completing the scan in the entire marked area.

It further comprises advancing the scanning path of the focal point of the convergent scanning device (100), with respect to the path of the second treatment device (300), wherein the second treatment device (300) have the same scanning path as the convergent scanning device (100) enabling the theranostic mode. (Simultaneous Diagnosis and Treatment)

Figure 33:
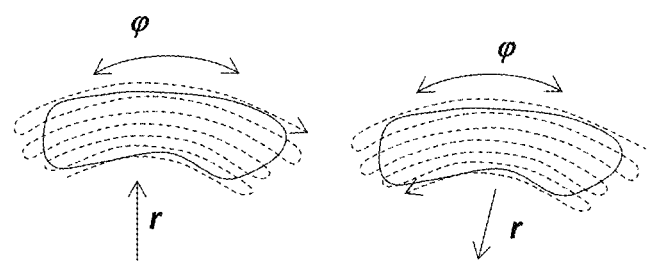
FIG. 33 shows zig-zag scanning/sweep scheme.
Figure 34:
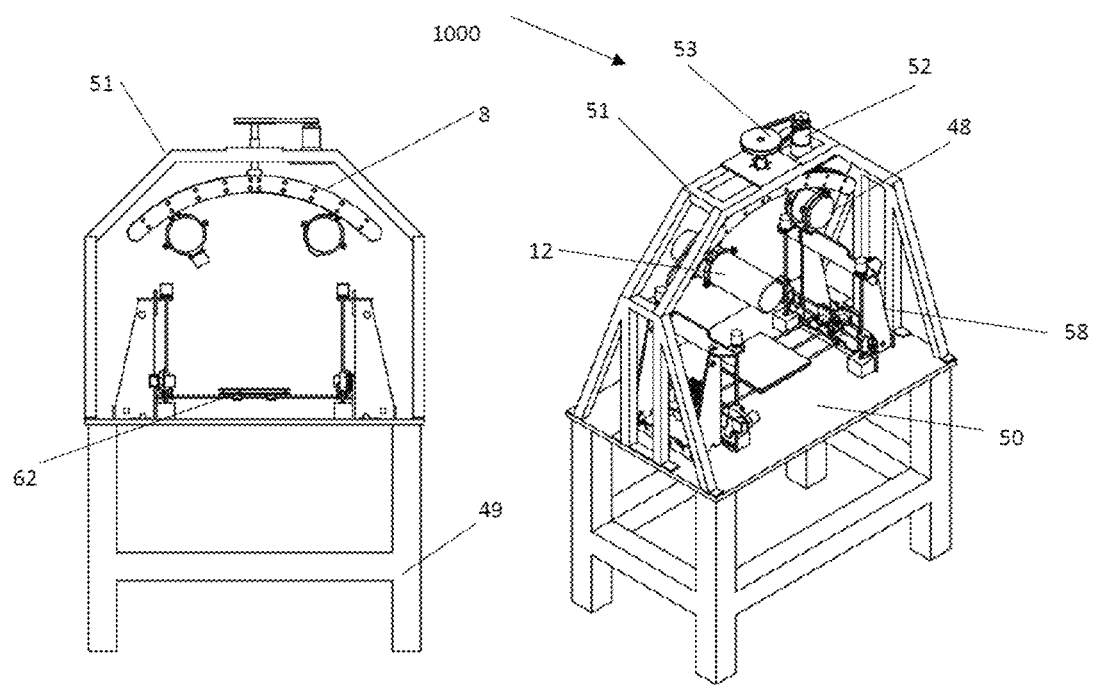
FIG. 34 shows an external Cartesian support structure that allows the installation of all the pieces and parts of this invention and the shielding.

Wherein, the three-dimensional sweep in the marked area comprises:
  a. performing helical paths (r, φ) or helix (r, φ) or concentric (r, φ) or zig-zag arcs (r, φ) or Cartesian (x, y) with the focal point of the devices (100 and 300) increasing or decreasing;
  b. longitudinally displacing the focal point of the devices (100 and 300), in the coordinate in (z or −z); and
  c. repeating steps a. and b. until the demarcated area is covered.
  (FIGS. 32 and 33 with 3D cylindrical radial scanning device)

The method of detecting, imaging, and treating or eliminating neoplasms further comprises:
  i. defining the scan paths through a computer 800 in a marked area and coordinating the reading of the fluorescent signals coming from the detection system with the position of the scanning, wherein the marked area comprises the volume of the anomalies and the variability of the displacement of these anomalies (neoplastic cells), wherein a first reading is associated with a spatial point of the scan area;
  ii. defining the pixel of the 3D image that is built as the scanning path evolves;
  iii. constructing a 3D matrix of fluorescent intensities and a 3D image of the tumor inside the scanning zone;
  iv. maintaining the scanning in the scanning zone with the convergent scanning device (100), to ensure the correct location of each spatial point of the anomalies (neoplastic cells) through a second reading associated with a spatial point of the scanning zone;
  v. immediately applying the convergent beam of the convergent device 300 in the volume detected with the biomarker following the paths in the volumes with fluorescent signal and annihilate or treat the anomalies (neoplastic cells) at the same biomarker points and excited by the first beam, where the focal point of the second beam of the convergent device (300) is out of phase/offset with respect to the point already scanned by the convergent scanning device (100);

vi. interrupting the convergent beam of the convergent device 300 when the detection system does not detect fluorescent signal through a fast triggering metal plate 41, to immediately apply the convergent beam of the convergent device (300) only when the detection system 200 detects fluorescent signal due to excitation of the biomarked cells, induced by the scanning convergent device (100);

vii. repeating steps iv to vi, until covering the entire treatment scan volume of the marked area defined by the spatial position of the volume comprising the anomalies and the variability of the displacement of said anomalies (neoplastic cells).

COMPONENT LIST

1. Electron gun.
2. Beam brake.
3. Conductive external cylinder.
4. White metallic inner cylinder.
5. Spherical poly-collimator.
6. Septa holes.
7. Confocal laser guides.
8. Supporting arch.
9. Shaft/Axis.
10. Bearings
11. Laser guide bar.
12. X-ray tube.
13. X-ray tube collimator
14. Counterweight
15. Clamp support
16. White curved cylinder
17. White conical ring
18. Long White Curved Conical Cylinder
19. Position holes
20. Long curved slot
21. Fixing bolt
22. Curved toothed slot
23. Electric motor tube position in the arc
24. Supportive straight arm
25. Angular fixing.
26. Angular electric motor.
27. Toothed straight slot.
28. Counterweight displacement electric motor/treatment tube.
29. Septa collimator detector.
30. X-ray detector.
30b. Detector support.
31. Pulse amplifier.
32. MCA pulse processor.
33. Confocal detector collimator with cylindrical septa
34. Confocal detector collimator with conical septa.
35. Collimator with honeycomb detector septa.
36. Flat base with grip holes
37. Confocal cadmium telluride detector with collimators
38. Large area detector (from 50 cm² or more).
39. Support base for multiple detectors
40. Convergent static treatment device
41. Metallic foil/sheet
42. Bidirectional solenoid.
43. Solenoid shaft
44. Shaft gate fixings
45. Spherical circular gate with holes.
46. Stepper motor opening/closing
47. Dynamic convergent treatment X-ray device
48. Collimator solenoid fixing
49. Supportive legs.
50. Structural flat base.
51. Arch support structure.
52. Driving electric motor
53. Reducer
54. Treatment X-ray tube support
55. Arch of essential supporting structure.
56. Fixing elements devices
57. Parallel joint with thread.
58. Base structure of commercial 3D printer
59. Encoder
60. Stepper motor 3D Cartesian system.
61. Rails
62. Stretcher.
63. Parallel motors for radial movement
64. Parallel guides with screw.
65. Curved structure
65B. Double ring sliding carriages
66. Double ring structural rail
67. Shielded external structure for ionizing radiation.
68. Reinforced door.
69. Braked wheels.
70. External boxes electronic control elements.
71. Shielded observation window.
72. Reducer motor box.
73. Union plate.
74. Fixings to plate and double ring to external structure.
75. Shielded cylindrical external structure.
76. Support base.
77. Conventional X-ray tube of the CAT (Computed Tomograph/Scanner)
78. TAC collimator system
79. X-ray detectors
80. Electronics associated with the TAC
81. Carriages for TAC movement
82. C structure of 180° TAC
83. Ring guide support
84. Toothed circular rail
85. Electric motor
100. Convergent scanning device
110. Static curved convergent device
120. Static ring convergent device
130. Static long curved convergent device
150. Dynamic convergent scanning device
200. Detection system
300. Fixed convergent treatment device
310. Fast gate
400. Supporting structure
410. Cartesian support structure
500. 3D motion structure
550. Cartesian 3D motion structure
570. Cylindrical 3D Motion Structure
600. Overall assembly
650. General assembly cylindrical version
700. Programmable Electronic System and Control Method
800. Computer
1000. Fluorescent confocal system
2000. Computerized tomography CT
3000. Device System for detecting, obtaining images and treating or removing neoplasms

The invention claimed is:

1. A system for detecting, obtaining images and treating or eliminating neoplasms, pathologies or other anomalies, which is excited through X-rays biomarked with metallic nanoparticles, the system comprising an external support structure with shielding comprising:
A. a confocal system comprising
   a shielded external structure housing a supporting structure comprising:
      a scanning X-ray convergent device;
      a detection system for X-ray with collimators solidary and confocal to the scanning X-ray convergent device;
      a second convergent processing device solidary to the scanning X-ray convergent device and the detection system for X-ray with collimators; and
   wherein the scanning X-ray convergent device, the detection system for X-ray with collimators and the second convergent device project to a single focal point and are confocal;
B. a controlled 3D scanning structure moving a stretcher and/or the single focal point where ionizing radiation is concentrated;
C. an electronic control system comprising programmable electronics that allow operation of the supporting structure containing the scanning X-ray convergent device, the detection system for X-ray with collimators and the second convergent processing device; and
D. a computerized tomography CT comprising collimators, X-ray tube and detectors incorporated in the external support structure with shielding.

2. The system according to claim 1, wherein the scanning X-ray convergent device comprises
   a vacuum static cylindrical convergent ionizing radiation device consisting of an electron gun,
   a beam braker,
   a white metallic cylinder of high Z>50 covered by a cylinder of a conductive material comprising Al or Cu,
   a spherical cap as a collimator with separate collimation holes pointing to the single focal point and confocal laser guides, and
   a curved anode cylinder, a curved anode ring, or a long curved anode cylinder.

3. The system according to claim 1, wherein the scanning X-ray convergent device comprises a dynamic convergent ionizing radiation scanning device consisting of
   a rotating support arc with a shaft,
   bearings,
   a bar with confocal laser guides,
   X-ray tube with a collimator and counterweight at one end of the collimator, wherein an X-ray output is collimated by means of the collimator pointing to the single focal point.

4. The system according to claim 2, wherein each of the collimator and the X-ray tube comprises angular electric motors that allow an angle of the collimator and an angle of the X-ray tube to be varied in a continuous mode;
   the rotating support arc with a shaft comprises a C-arc, position adjustment means on the C-arc that allow fixing the X-ray tube directed to the collimated output pointing towards the single focal point, and second electric motors corresponding to the collimator and the X-ray tube which allow movement along the C-arc of the rotating support arc with a shaft.

5. The system according to claim 1, wherein the supporting structure is a supporting arch or a straight arm.

6. The system according to claim 4, wherein the angles of the collimator and the X-ray tube are generated in preset positions without changing the position of the single focal point; and
   wherein the position adjustment means are selected from positional holes, a long curved slot, a curved toothed slot or a straight toothed slot allowing an angle of the convergent cone to be varied.

7. The system according to claim 1, wherein the detection system for X-ray with collimators comprises one or more confocal septa attached to an input of an X-ray detector, an amplification system and MCA multichannel pulse processor,
   wherein the one or more confocal septa is straight, cylindrical, conical septa or conical honeycombed hexagonal septa, and
   wherein the X-ray detector comprises one or more solid state detectors, selected from cadmium telluride (CdTe) on support or hyper pure Germanium (Ge) or NaI (Tl) sodium iodide scintillator.

8. The system according to claim 7, wherein the detection system for X-ray with collimators is formed by at least two X-ray detectors that are confocal, with an area greater than 0.25 cm$^2$, configured concentrically, until covering an entire visible area of radiation output of an object to be analyzed in an isotropic manner.

9. The system according to claim 1, wherein the second convergent processing device has higher power than the scanning X-ray convergent device,
   the scanning X-ray convergent device uses energy in an orthovoltage range of 100-750 keV, alternatively uses energy in a soft X-ray range of less than 100 keV, for superficial applications, and
   wherein the scanning X-ray convergent device has a dual function of a first operation in scan mode marking an area with a power of at most 50 W and a second operation in therapy mode by increasing an operating current with a power of at least 100 W.

10. The system according to claim 1, wherein the second convergent processing device comprises a fast gate comprising at least one metallic foil attached to a bidirectional solenoid which moves the foil to output a beam only when there is fluorescent signal recorded by the detection system for X-ray with collimators, wherein the at least one metallic foil is permanently interrupting the beam to completely attenuate the beam <1% when no fluorescent signal is recorded.

11. The system according to claim 1, wherein the scanning X-ray convergent device or the second convergent processing device comprises a spherical circular gate with a plurality of holes and a spherical poly collimator comprising a plurality of holes, the plurality of holes of the spherical circular gate correspond with the plurality of holes of the spherical poly collimator,
   wherein the circular spherical gate rotates angularly and concentrically to an axis of the scanning X-ray convergent device or the second convergent processing device, to open a passage of radiation beams, through a stepper motor, which is permanently closed when fluorescent signal is not detected.

12. The system according to claim 1, wherein the shielded external structure housing the supporting structure further comprises a Cartesian support structure for 3D Cartesian scanning formed by a flat base with grip holes for detector supports, and opposite to the flat base holding the supporting structure with the scanning X-ray convergent device to generate the convergent scanning beam which allows micro displacements in the X, Y plane, and
   a 3D Cartesian displacement structure comprising a first set of rails for linear displacement in the X, Y planes, and a second set of rails for vertical displacement in the Z plane to perform the Cartesian movement.

13. The system according to claim 12, wherein the 3D Cartesian displacement structure further comprises a third set of rails for linear displacement in the X plane and a fourth set of rails for linear vertical displacement in the Z plane and means for angular displacements.

14. The system according to claim 12, wherein the shielded external structure is mounted above the Cartesian support structure, wherein the shielded external structure comprises a shielded door, a shielded observation window and/or a set of cameras.

15. The system according to claim 1, wherein the supporting structure further comprises a double ring structural rail with connecting plates, which supports a curved structure with carriages attached parallel to the supporting structure by means of two parallel joints with thread and motors such that movements of the supporting structure is carried out in radial ($\rho$), angular ($\varphi$), and longitudinal (z) directions.

16. The system according to claim 15, comprising a general control unit interfacing with:
   a circuit of detectors that control the detection system for X-ray with collimators;
   a trigger control circuit, to control at least one bidirectional solenoid and let a treatment beam pass;
   convergent device control circuits for controlling the scanning X-ray convergent device; and
   3D motion circuit to control the motors,
   wherein said circuits are controlled by a central processing and communication unit.

17. The system according to claim 1, further comprising a computed tomograph comprising:
   a conventional X-ray tube,
   a system of collimators and
   detectors within a fluorescent confocal system,
   wherein the fluorescent confocal system and the computed tomograph are connected by means of a ring guide support to a double ring structural rail,
   wherein the shielded external structure is solidly attached to a base wherein the ring guide support movably joins the shielded external structure with respect to the double ring structural rail, allowing the double ring structural rail to rotate 360°, in a controlled manner, the fluorescent confocal and the computerized tomography.

18. The system according to claim 1, wherein the single focal point of the scanning X-ray convergent device, the detection system and the second convergent processing device advances in its scanning path allowing a theranostic mode of simultaneous diagnosis and treatment.

19. A method of detecting, obtaining images and treating or eliminating of neoplasms, pathologies or other anomalies, which is excited through X-rays biomarked with metallic nanoparticles using the system of claim 1, the method comprising the steps of:
   A. capturing anatomical images of the individual ("fantoma", animal, person) to detect any anomaly, by means of a CT scanner which is inside an external support structure;
   B. when any anomaly is detected marking an area of the individual and analyzing the area with biomarker means through the confocal system of claim 1; and
   C. when biomarker X-ray fluorescence signal is detected by detection system, applying convergent treatment device, wherein convergent treatment device applies radiation at the three-dimensional coordinates that the scanning X-ray convergent device generated X-ray fluorescence detected by detection system.

20. The method according to claim 19, comprising repeating step C, until the sweep is completed over the entirety of the marked area.

21. The method according to claim 19, comprising advancing the scanning path of the focal point of the scanning X-ray convergent device, relative to the path of the second convergent processing device, wherein the second convergent processing device has the same scanning path as the scanning X-ray convergent device enabling a theranostic mode of simultaneous diagnosis and treatment.

22. The method according to claim 19, wherein a three-dimensional scan in a marked area comprises:
   a. performing helical (r, $\varphi$) or helix (r, $\varphi$) or concentric (r, $\varphi$) or zig-zag arcs (r, $\varphi$) or Cartesian (x, y) with the single focal point of the scanning X-ray convergent device and the second convergent processing device increasing or decreasing;
   b. longitudinally displacing the single focal point of the scanning X-ray convergent device and the second convergent processing device, in a coordinate in z or −z; and
   c. repeating steps a. and b. until a demarcated area is covered.

23. The method according to claim 19, comprising:
   i. defining a scan paths through a computer in a marked area and coordinating a reading of fluorescent signals coming from the detection system with a position of the scanning, wherein the marked area comprises a volume of anomalies and variability of displacement of these anomalies, wherein a first reading is associated with a spatial point of a scan area;
   ii. defining a pixel of a 3D image that is built as the scanning path evolves;
   iii. constructing a 3D matrix of fluorescent intensities and a 3D image of a tumor inside a scanning zone;
   iv. maintaining the scanning in the scanning zone with the scanning X-ray convergent device, to ensure correct location of each spatial point of the anomalies through a second reading associated with a spatial point of the scanning zone;
   v. immediately applying a convergent beam of the second convergent processing device in the volume detected with the biomarker following the paths in the volumes with fluorescent signal and annihilate or treat the anomalies at the same biomarker points and excited by a first beam, where the focal point of a second beam of the second convergent processing device is out of phase/offset with respect to the point already scanned by the scanning X-ray convergent device;
   vi. interrupting the convergent beam of the second convergent processing device when the detection system does not detect fluorescent signal through a fast triggering metal plate, to immediately apply the convergent beam of the second convergent processing device only when the detection system detects fluorescent signal due to excitation of the biomarked cells, induced by the scanning X-ray convergent device;
   vii. repeating steps iv to vi, until covering the entire treatment scan volume of the marked area defined by the spatial position of the volume comprising the anomalies and the variability of the displacement of said anomalies.

\* \* \* \* \*